US011529329B2

(12) United States Patent
Schou

(10) Patent No.: US 11,529,329 B2
(45) Date of Patent: Dec. 20, 2022

(54) POWDERED COMPOSITION COMPRISING A COMPLEX BETWEEN A CANNABINOID AND A BASIC ION EXCHANGE RESIN

(71) Applicant: NordicCan A/S, Vejle (DK)

(72) Inventor: Søren Christian Schou, Herning (DK)

(73) Assignee: NORDICCAN A/S, Vejle (DK)

( * ) Notice: Subject to any disclaimer, the term of this patent is extended or adjusted under 35 U.S.C. 154(b) by 731 days.

(21) Appl. No.: 16/304,038

(22) PCT Filed: May 27, 2016

(86) PCT No.: PCT/DK2016/050157
§ 371 (c)(1),
(2) Date: Nov. 21, 2018

(87) PCT Pub. No.: WO2017/202424
PCT Pub. Date: Nov. 30, 2017

(65) Prior Publication Data
US 2020/0316012 A1  Oct. 8, 2020

(51) Int. Cl.
| *A61K 9/00* | (2006.01) |
| *A61K 31/05* | (2006.01) |
| *A61K 47/30* | (2006.01) |
| *A61K 31/352* | (2006.01) |
| *A61K 9/68* | (2006.01) |

(52) U.S. Cl.
CPC .......... *A61K 31/352* (2013.01); *A61K 9/0056* (2013.01); *A61K 9/0058* (2013.01); *A61K 31/05* (2013.01); *A61K 47/30* (2013.01)

(58) Field of Classification Search
CPC .. A61K 2300/00; A61K 31/05; A61K 31/352; A61K 45/06; A61K 47/30; A61K 47/32; A61K 9/0056; A61K 9/0058; A61K 9/146; A61K 9/2013; A61K 9/2018; A61K 9/2027; A61K 9/2054; A61K 9/2077; A61P 1/14; A61P 25/04
See application file for complete search history.

(56) References Cited

U.S. PATENT DOCUMENTS

| 8,906,429 | B1 | 12/2014 | Kolsky | |
| 2005/0153931 | A1* | 7/2005 | Jarho | ...................... A61P 21/00 |
| | | | | 514/58 |
| 2005/0181050 | A1* | 8/2005 | Hirsh | ................... A61K 47/585 |
| | | | | 424/469 |
| 2015/0064250 | A1 | 3/2015 | Ghebre-Sellassie et al. | |
| 2016/0015683 | A1 | 1/2016 | McCarty | |
| 2019/0060229 | A1* | 2/2019 | Neergaard | ........... A61K 9/1635 |

FOREIGN PATENT DOCUMENTS

| WO | WO2002064109 A2 | 8/2002 |
| WO | WO2009120080 A1 | 10/2009 |

OTHER PUBLICATIONS

Anderson et al. (Industrial and Engineering Chemistry 1955;47(1): 71-75) (Year: 1955).*
Suhagiya et al. (IJPSR 2010;1(4):22-37) (Year: 2010).*
Powder from the Free Dictionary ([online] retrieved from: https://medical-dictionary.thefreedictionary.com/powder; on Jul. 29, 2021; 3 pages) (Year: 2021).*
Amberlite Ion Exchange Resins ([online] retrieved on Apr. 26, 2022 from: https://inaqua.de/assets/Fusion-Dow-DuPont/AMBERLITE-IX-Portfolio-INAQUA.pdf; 22 pages) (Year: 2022).*
Amberlite and Duolite [online] retrieved on Apr. 26, 2022 from: https://www.pp.pharma.dupont.com/pharmaceutical-brands/amberlite-and-duolite.html; 2 pages) (Year: 2022).*
Guo et al., "Ion-exchange resins as drug delivery carriers," Nov. 2009, Journal of Pharmaceutical Sciences. 98 (11): 3886-3902.
Hendriks et al., "Use of Amberlite XAD-2 columns for the separation of cannabinoids from Cannabis extracts," Jan. 19, 1981, Journal of Chromatography. 205(2):444-450.
International Search Report dated Mar. 2, 2017 in International Application No. PCT/DK2016/050157, 12 pages.
PCT: International Preliminary Report on Patentability of PCT/DK2016/050157; Simin Baharlou; Nov. 27, 2018; 7 pages.

* cited by examiner

*Primary Examiner* — Ernst V Arnold

(57) ABSTRACT

A powdered composition is disclosed, the powdered composition comprising a complex between one or more cannabinoids having at least one phenolic moiety and a basic ion exchange resin. Also, an orally dispensable delivery vehicle, a method of manufacturing the powdered composition, a method of manufacturing the orally dispensable delivery vehicle, composition for use as a medicament, composition for use in a treatment, method of treatment, and use of a basic ion exchange resin as a stabilizing agent are disclosed.

21 Claims, No Drawings

POWDERED COMPOSITION COMPRISING A COMPLEX BETWEEN A CANNABINOID AND A BASIC ION EXCHANGE RESIN

CROSS REFERENCE TO RELATED APPLICATIONS

This application is a U.S. National Phase Application of International Application No. PCT/DK2016/050157, filed May 27, 2016, which is hereby incorporated by reference in their entirety.

FIELD OF THE INVENTION

The invention relates to administration of cannabinoids in oral formulations and in particular to a complex between cannabinoids and a basic ion exchange resin used in oral administration.

BACKGROUND OF THE INVENTION

Cannabinoids or derivatives thereof have been used for medical purposes. However, one problem related thereto is that some cannabinoids are oxidized relatively fast once they have been removed from cannabis.

Thus, cannabis is often administering by smoking. A problem related to such administration is that the rapid absorption into the blood via the lung may be undesirable. Not only may the smoking as such have side effects, but the administration may be difficult to manage.

SUMMARY OF THE INVENTION

The invention relates to a powdered composition comprising a complex between one or more cannabinoids having at least one phenolic moiety and a basic ion exchange resin.

One very significant advantage of the present invention may be that the one or more cannabinoids are provided in a relatively stable and flexible form, which can be utilized in a wide range of orally dispensable delivery vehicle applications while achieving a rather effective stabilization and long lifetime.

It is also noted that the use of a basic ion exchange resin facilitates the release of the cannabinoid from the basic ion exchange resin when used as an oral composition, thereby activating the cannabinoid for uptake into the body. The activation may thus e.g. be obtained through the saliva of the oral cavity or in advantageous embodiments this may be obtained by adding acids as a pH controlling agent to the oral composition.

Also, a significant advantage of the invention may be that while achieving high stability and flexibility of the composition itself, the desirable stability may be retained while incorporating the composition in various suitable orally dispensable delivery vehicles.

The composition according to an embodiment of the invention may also have the advantage that this composition due to the stable nature is advantageous for use in delivery vehicles which has the ability of administering the release and resulting activation of the cannabinoid over time, thereby obtaining an improved and advantageous bioavailability of the cannabinoid in question.

A further important advantage of the invention may be that while the composition has a very desirable stability retainable in orally dispensable delivery vehicles, such delivery vehicles be operable with a synchronized release of flavor and/or taste masking agents giving the user a desirable experience while delivering an effective amount of the cannabinoid(s) to the user. This may be achieved since the stabilization may be provided without stabilization agents resulting in an unpleasant or distasteful experience for the user. Since the composition is provided as a powder, it is prepared for immediate incorporation in dry delivery vehicles for oral administration; thus, the composition can readily be combined with pH controlling acids, without leading to any substantial pre-release (and hence pre-degradation). In other words, the composition allows for a synchronized release of pH controlling acids for facilitating release of cannabinoid(s) from the complex with the basic ion exchange resin.

One further advantage of the invention may be that by providing the composition as a powdered composition, it may be included in a variety of oral delivery vehicles adapted for releasing the cannabinoid(s), and optionally further ingredients, in the oral cavity, which in turn facilitates uptake of the cannabinoid(s) in the oral cavity via the oral mucosa, thereby bypassing the first-pass metabolism.

A further advantage of the invention may be that while achieving a combination of suitably stability of the cannabinoid(s) and easy activation thereof for body uptake, the powdered composition provides mixability, which may help to ensure that that the cannabinoid(s) can be distributed relatively evenly throughout an orally dispensable delivery vehicle thus ensuring a desired release and activation for body uptake of the cannabinoid(s).

As used herein the term "complex" is to be understood as a chemical association of two or more species (as ions or molecules) joined usually by electrostatic or ionic bonds rather than covalent bonds.

In the present context, where the terms "the composition" or "said composition" are used without any specific link, these terms are intended to refer to the powdered composition of the invention.

The cannabinoid(s) used according to the invention may be of different types, and may be a mixture of two or more different cannabinoids, or a single cannabinoid; however, only cannabinoids having at least one phenolic moiety can be used. Thus, cannabinoids having two or more phenolic moieties may be used. Further, also cannabinoids having one or more carboxylic acid moieties may be used as long as they also have at least one phenolic moiety.

By using cannabinoid(s) having at least one phenolic moiety, the basic group of the basic ion exchange resin has one or more groups on the cannabinoid(s) to bind with. The cannabinoid(s) may in some embodiment optionally comprise one or more carboxylic groups, thus adding to the potential binding sites for the basic ion exchange resin.

In the present context, when the content of the powdered composition is specified, for example in percent by weight, the percent by weight is relative to the powdered composition, unless otherwise stated. Similarly, if other contents are specified, any weight percent is relative to that of which the content is being specified, unless otherwise stated.

Thus, it should be understood that in accordance with the present invention, the powdered composition may in some embodiments comprise only a singly cannabinoid, i.e. a single type of cannabinoid, while in other embodiments the powdered composition may comprise a combination of two or more different types of cannabinoids.

In an embodiment of the invention the ion exchange resin(s) acts as a stabilization agent.

One very important advantage of the above embodiment may be that the amount of cannabinoid(s) available for body uptake is advantageously preserved due to the stabilization of the cannabinoid(s). Also, a more appealing orally dispensable delivery vehicle may be obtained by use of the powdered composition of the above embodiments due to countering of discoloration of the cannabinoid(s).

In an advantageous embodiment of the invention the basic ion exchange resin comprises strongly basic ion exchange resin.

One advantage of the above embodiment may be that a relatively effective stabilization of the cannabinoid(s) may be achieved, while synchronized release of the cannabinoid(s) from the complex, i.e. synchronized with the intended time of delivery to the body may be achieved, e.g. in one embodiment by adding an acid to an orally dispensable delivery vehicle comprising the powdered composition.

In an advantageous embodiment of the invention the basic ion exchange resin is strongly basic ion exchange resin.

One advantage of the above embodiment may be that a relatively effective stabilization of the cannabinoid(s) may be achieved, while synchronized release of the cannabinoid(s) from the complex, i.e. synchronized with the intended time of delivery to the body may be achieved, e.g. in one embodiment by adding an acid to an orally dispensable delivery vehicle comprising the powdered composition.

In an advantageous embodiment of the invention the basic ion exchange resin comprises weakly basic ion exchange resin.

One advantage of the above embodiment may be that a relatively effective release of the cannabinoid(s) from the complex may be obtained, in some embodiments without using any agents, such as acids, for facilitating release of the cannabinoid(s) from the complex.

In an advantageous embodiment of the invention said basic ion exchange resin is a strongly basic ion exchange resin comprising one or more quaternary amino groups.

Examples of strongly basic ion exchange resins include for example commercially available products, such as Ambersep® 900, Cholestyramine, and Duolite AP143.

In an advantageous embodiment of the invention the basic ion exchange resin are selected from the group consisting of Ambersep 900, Cholestyramine, Duolite AP143, Amberlite CG-400, Amberlite IRA-400, Amberlite IRA-401, Amberlite IRA-410, Amberlite IRA-900, and Amberlite IRA-904.

In an advantageous embodiment of the invention the basic ion exchange resin comprises cross-linked polystyrene.

In an advantageous embodiment of the invention the basic ion exchange resin comprises cross-linked polystyrene, wherein the cross-linking agent comprises or is divinylbenzene.

In an advantageous embodiment of the invention the basic ion exchange resin comprises a styrene-divinylbenzene copolymer.

According to an embodiment of the invention, the basic ion exchange resin is a styrene-divinylbenzene copolymer functionalized by basic groups, such as amine groups. If a strongly basic ion exchange resin is desirable, strongly basic functional groups, such as quaternary amines, are used; whereas if a weakly basic ion exchange resin is desirable, weakly basic functional groups, such a primary, secondary, or tertiary amine groups, are used.

In an advantageous embodiment of the invention the basic ion exchange resin has a counter ion selected from the group consisting of hydroxide, chloride, and bromide, before reaction with the one or more cannabinoids.

In an advantageous embodiment of the invention the loading of the basic ion exchange resin is between 5 percent and 95 percent.

One advantage of the above embodiment may be that by adjusting the loading of the basic ion exchange resin to the desired value, an advantageous mixability may be obtained while keeping the amount of basic ion exchange resin in an orally dispensable delivery vehicle below a desired value, e.g. due to a desired size or weight of the final orally dispensable delivery vehicle.

In the present context it should be understood that the term "loading" is intended to mean the content of said one or more cannabinoids as a percentage by weight of the powdered composition In an embodiment of the invention the loading of the basic ion exchange resin is between 5 percent and 70 percent.

In an embodiment of the invention the loading of the basic ion exchange resin is between 5 percent and 50 percent.

In an embodiment of the invention the loading of the basic ion exchange resin is between 5 percent and 20 percent.

In an embodiment of the invention the loading of the basic ion exchange resin is between 10 percent and 15 percent.

In an advantageous embodiment of the invention said composition comprises at least two cannabinoids.

In an advantageous embodiment of the invention said composition comprises two cannabinoids, and wherein the composition is substantially free of further cannabinoids other than said two cannabinoids.

Thus, it should be understood according to the above embodiment that the composition comprises a combination of two cannabinoids, i.e. a combination of two different types of cannabinoids. Thus, the composition according to the above embodiment comprises only two cannabinoids. In practical scenarios, it may not be easy to achieve complete elimination of certain substances, thus, there may in some embodiments be small or trace amounts of further cannabinoids, e.g. due to a small degree of degradation of the intended cannabinoid(s).

In an advantageous embodiment of the invention said one or more cannabinoids are derived from cannabis.

In an alternative embodiment, the composition may comprise one or more cannabinoids, where one or all of the cannabinoids are not derived from cannabis, e.g. synthetic cannabinoids.

In an advantageous embodiment of the invention the one or more cannabinoids comprises THC.

In an advantageous embodiment of the invention the one or more cannabinoids comprises THC in an amount of between 10 and 100 percent by weight of the one or more.

In an embodiment of the invention the one or more cannabinoids comprises THC in an amount of between 20 and 100 percent by weight of the one or more cannabinoids.

In an embodiment of the invention the one or more cannabinoids comprises THC in an amount of between 30 and 90 percent by weight of the one or more cannabinoids.

In an embodiment of the invention the one or more cannabinoids comprises THC in an amount of between 50 and 90 percent by weight of the one or more cannabinoids.

In an embodiment of the invention the one or more cannabinoids comprises THC in an amount of between 70 and 80 percent by weight of the one or more cannabinoids.

In an advantageous embodiment of the invention the one or more cannabinoids comprises CBD.

In an advantageous embodiment of the invention the one or more cannabinoids comprises CBD in an amount of between 10 and 100 percent by weight of the one or more cannabinoids.

In an embodiment of the invention the one or more cannabinoids comprises CBD in an amount of between 20 and 100 percent by weight of the one or more cannabinoids.

In an embodiment of the invention the one or more cannabinoids comprises CBD in an amount of between 30 and 90 percent by weight of the one or more cannabinoids.

In an embodiment of the invention the one or more cannabinoids comprises CBD in an amount of between 50 and 90 percent by weight of the one or more cannabinoids.

In an embodiment of the invention the one or more cannabinoids comprises CBD in an amount of between 70 and 80 percent by weight of the one or more cannabinoids.

In an advantageous embodiment of the invention the one or more cannabinoids are selected from the group consisting of THC, CBD, and CBN.

The one or more cannabinoids may also include any combination of the mentioned cannabinoids.

THC may refer to Tetrahydrocannabinol, (−)-trans-$\Delta^9$-tetrahydrocannabinol (IUPAC: (−)-(6aR,10aR)-6,6,9-Trimethyl-3-pentyl-6a,7,8,10a-tetrahydro-6H-benzo[c]chromen-1-ol)

CBD may refer to Cannabidiol (IUPAC: 2-[(1R,6R)-6-isopropenyl-3-methylcyclohex-2-en-1-yl]-5-pentylbenzene-1,3-diol).

CBN may refer to Cannabinol (IUPAC: 6,6,9-Trimethyl-3-pentyl-benzo[c]chromen-1-ol).

CBC may refer to Cannabichromene (IUPAC: 2-Methyl-2-(4-methylpent-3-enyl)-7-pentyl-5-chromenol).

In an advantageous embodiment of the invention said one or more cannabinoids comprises one or more cannabinoids selected from the group consisting of THC, CBD, and CBN in an amount of between 10 and 100 percent by weight of said one or more cannabinoids.

In an embodiment of the invention said one or more cannabinoids comprises one or more cannabinoids selected from the group consisting of THC, CBD, and CBN in an amount of between 20 and 100 percent by weight of said one or more cannabinoids.

In an embodiment of the invention said one or more cannabinoids comprises one or more cannabinoids selected from the group consisting of THC, CBD, and CBN in an amount of between 30 and 90 percent by weight of said one or more cannabinoids.

In an embodiment of the invention said one or more cannabinoids comprises one or more cannabinoids selected from the group consisting of THC, CBD, and CBN in an amount of between 50 and 90 percent by weight of said one or more cannabinoids.

In an embodiment of the invention said one or more cannabinoids comprises one or more cannabinoids selected from the group consisting of THC, CBD, and CBN in an amount of between 70 and 80 percent by weight of said one or more cannabinoids.

In an advantageous embodiment of the invention the composition is substantially free of cannabinoids other than said one or more cannabinoids.

In an advantageous embodiment of the invention the one or more cannabinoids consist substantially of THC.

In an advantageous embodiment of the invention the one or more cannabinoids consist substantially of CBD.

In an advantageous embodiment of the invention the one or more cannabinoids consist substantially of a combination of THC and CBD.

In an embodiment said one or more cannabinoids comprises tetrahydrocannabinol (THC).

Preferably THC is intended to mean (−)-trans-$\Delta^9$-tetrahydrocannabinol, i.e. (6aR,10aR)-delta-9-tetrahydrocannabinol).

In an embodiment of the invention said one or more cannabinoids comprises cannabidiol (CBD).

According to an embodiment, the CBD is or comprises $\Delta^1$-cannabidiol.

In an embodiment of the invention said one or more cannabinoids comprises a combination of several cannabinoids, such as THC and CBD.

In an embodiment of the invention said one or more cannabinoids is THC.

In an embodiment of the invention said one or more cannabinoids is CBD.

In an embodiment of the invention said one or more cannabinoids is a combination of THC and CDB.

In an advantageous embodiment of the invention the one or more cannabinoids comprises THC, CBD, CBN, derivatives thereof, including analogues and homologues.

In an advantageous embodiment of the invention the cannabinoid is selected from cannabinoids having the following structure

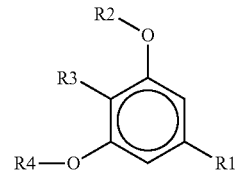

where R1 is an alkyl comprising at least 4 carbon and having a longest chain of at least 4 carbons, where R2 is selected from hydrogen, hydrocarbon, and functionalized hydrocarbon, where R3 is an hydrocarbon, and functionalized hydrocarbon, where R4 is selected from hydrogen, hydrocarbon, and functionalized hydrocarbon, where at least one of R2 and R4 is hydrogen, where R2 or R4 may be connected to R3 to form R2-R3 or R4-R3, respectfully.

In an advantageous embodiment of the invention the composition further comprises one or more aid substance(s).

In an embodiment said one or more aid substances comprises one or more organic polyol(s). The organic polyol may be a non-toxic C2 to C12 linear or branched hydrocarbon having at least two hydroxy groups or it may be a non-toxic C5 to C12 cyclic or heterocyclic hydrocarbon having at least two hydroxy groups. The former compounds are illustrated by the polyhydric alcohols such as 1,3-dihydroxypropane, hexylene glycol, glycerin, sorbitol etc., the latter by inositol and the carbohydrates such as glucose, sucrose, etc.

In one embodiment the aid substances may comprise polyols such as glycerin.

In an advantageous embodiment of the invention the powdered composition comprises said one or more aid substance(s) in amounts of between 1 and 70 percent by weight of the powdered composition.

In an embodiment of the invention the powdered composition comprises said one or more aid substance(s) in amounts of between 2 and 50 percent by weight of the powdered composition.

In an embodiment of the invention the powdered composition comprises said one or more aid substance(s) in amounts of between 5 and 40 percent by weight of the powdered composition.

In an embodiment of the invention the powdered composition comprises said one or more aid substance(s) in amounts of between 10 and 30 percent by weight of the powdered composition.

In an advantageous embodiment of the invention said composition comprises said complex in an amount of between 30 and 100 percent by weight of the powdered composition.

Thus, in one embodiment of the invention, the powdered composition consists substantially of said complex.

In an embodiment of the invention said composition comprises said complex in an amount of between 40 and 99 percent by weight of the powdered composition.

In an embodiment of the invention said composition comprises said complex in an amount of between 50 and 95 percent by weight of the powdered composition.

In an embodiment of the invention said composition comprises said complex in an amount of between 60 and 90 percent by weight of the powdered composition.

In an embodiment of the invention said composition comprises said complex in an amount of between 60 and 80 percent by weight of the powdered composition.

In one embodiment of the invention, the powdered composition consists substantially of said complex in combination with one or more aid substance(s), where the aid substances may comprise or consist of polyols, such as glycerin.

In an advantageous embodiment of the invention said powdered composition has a water content of less than 10 percent by weight of the composition.

Thus, the composition may in some embodiments be free or substantially free of water.

In an embodiment of the invention said powdered composition has a water content of less than 5 percent by weight of the composition.

In an embodiment of the invention said powdered composition has a water content of less than 2 percent by weight of the composition.

According to an embodiment, the powdered composition comprises water in an amount of between 0.1 and 10 percent by weight of the powdered composition, such as between 0.5 and 5 percent by weight of the powdered composition, such between 1 and 2 percent of the powdered composition.

According to an embodiment, the powdered composition comprises water in an amount of between 0.1 and 10 percent by weight of the powdered composition.

According to an embodiment, the powdered composition comprises water in an amount of between 0.5 and 5 percent by weight of the powdered composition.

According to an embodiment, the powdered composition comprises water in an amount of between 1 and 2 percent of the powdered composition.

In an advantageous embodiment of the invention said complex is present in amounts of at least 50 percent by weight of the powdered composition.

In an embodiment of the invention said complex is present in amounts of at least 70 percent by weight of the powdered composition.

In an embodiment of the invention said complex is present in amounts of at least 80 percent by weight of the powdered composition.

In an embodiment of the invention said complex is present in amounts of at least 90 percent by weight of the powdered composition.

In one embodiment, the complex is present in amounts of between 50 and 99 percent by weight of the composition.

In one embodiment, the complex is present in amounts of between 60 and 95 percent by weight of the composition.

In one embodiment, the complex is present in amounts of between 70 and 90 percent by weight of the composition.

In an advantageous embodiment of the invention said one or more cannabinoids are present in amounts of at least 1 percent by weight of the powdered composition.

In an embodiment of the invention said one or more cannabinoids are present in amounts of at least 5 percent by weight of the powdered composition.

In an embodiment of the invention said one or more cannabinoids are present in amounts of at least 10 percent by weight of the powdered composition.

In an embodiment of the invention said one or more cannabinoids are present in amounts of at least 15 percent by weight of the powdered composition.

In some embodiments, the cannabinoids are present in amounts of between 1 and 50 percent by weight of the powdered composition.

In some embodiments, the cannabinoids are present in amounts of between 2 and 30 percent by weight of the powdered composition.

In some embodiments, the cannabinoids are present in amounts of between 2 and 20 percent by weight of the powdered composition.

In some embodiments, the cannabinoids are present in amounts of between 3 and 10 percent by weight of the powdered composition.

In some embodiments, the cannabinoids are present in amounts of between 5 and 20 percent by weight of the powdered composition.

In some embodiments, the cannabinoids are present in amounts of between 10 and 20 percent by weight of the powdered composition.

In an advantageous embodiment of the invention said ion exchange resin(s) is present in amounts of at least 50 percent by weight of the composition.

In an embodiment of the invention said ion exchange resin(s) is present in amounts of at least 70 percent by weight of the composition.

In an embodiment of the invention said ion exchange resin(s) is present in amounts of at least 90 percent by weight of the composition.

In one embodiment, the ion exchange resin(s) is present in amounts of between 50 and 99 percent by weight of the composition.

In one embodiment, the ion exchange resin(s) is present in amounts of between 70 and 98 percent by weight of the composition.

In one embodiment, the ion exchange resin(s) is present in amounts of between 80 and 98 percent by weight of the composition.

In one embodiment, the ion exchange resin(s) is present in amounts of between 90 and 97 percent by weight of the composition.

In an advantageous embodiment of the invention said complex is formed by bonding of the ion exchange resin to one or more phenolic moiety of said one or more cannabinoids.

In an advantageous embodiment of the invention the average particle size of said powdered composition is between 1 and 400 micrometer.

In an embodiment of the invention the average particle size of said powdered composition is between 2 and 200 micrometer.

In an embodiment of the invention the average particle size of said powdered composition is between 5 and 100 micrometer.

In an embodiment of the invention the average particle size of said powdered composition is between 10 and 80 micrometer.

In an advantageous embodiment of the invention at least 50 percent by weight of said powdered composition has a particle size between 1 and 400 micrometer.

In an embodiment of the invention at least 75 percent by weight of said powdered composition has a particle size between 5 and 100 micrometer.

In an advantageous embodiment of the invention said complex comprises a combination of two or more cannabinoids.

Here, the complex comprising a complex of two or more cannabinoids may be one fraction of complex comprising a combination of two or more cannabinoids, or a mixture of two or more fractions, each fraction having complex comprising one or more cannabinoids. Thus, for example, the composition may comprise a first complex according to the invention comprising a first cannabinoid and further comprise a second complex according to the invention comprising a second complex according to the invention comprising a second cannabinoid, where the first cannabinoid is different from the second cannabinoid.

In an advantageous embodiment of the invention the powdered composition is adapted to release at least 50 percent by weight of said cannabinoids after 10 minutes.

In an embodiment of the invention the powdered composition is adapted to release at least 60 percent by weight of said cannabinoids after 10 minutes.

In an embodiment of the invention the powdered composition is adapted to release at least 70 percent by weight of said cannabinoids after 10 minutes.

In an embodiment of the invention the powdered composition is adapted to release at least 80 percent by weight of said cannabinoids after 10 minutes.

By releasing said one or more cannabinoids, the cannabinoid complex must dissolve into the saliva of the oral cavity in accordance with the above embodiment or in another environment, such as an environments emulation to some degree the oral environment, e.g. by setting a certain pH value. In some embodiments, this may also be in the presents of e.g. an acid suitable for being released from an orally dispensable delivery vehicle. Also, according to the above embodiments, the one or more cannabinoids is released from the complex in the amounts stated above. If testing in the oral cavity, i.e. by oral use, the oral use may naturally differ, e.g. according to the specific orally dispensable delivery vehicle. To illustrate this, when the orally dispensable delivery vehicle is a chewing gum the oral use is chewing, when the orally dispensable delivery vehicle is a lozenge or fast dissolving tablet the oral us may be sucking or gentle sucking.

In an advantageous embodiment of the invention at least 5 percent by weight of the powdered composition dissolves after 10 minutes.

In an embodiment of the invention at least 10 percent by weight of the powdered composition dissolves after 10 minutes.

In an embodiment of the invention at least 20 percent by weight of the powdered composition dissolves after 10 minutes.

In an embodiment of the invention at least 30 percent by weight of the powdered composition dissolves after 10 minutes.

For example, the degree of release or dissolution may be measured as an in vitro release or dissolution, respectfully, as determined by USP Type II apparatus, rotating paddle, with 900 milliliter of Phosphate buffer at pH 7.4, at a temperature of about 37 degrees Celsius, and set at rotating speed of 75 rpm. In another example, the degree of dissolution may be measured as an in vitro dissolution as determined by USP Type I apparatus, basket, with 900 ml of Phosphate buffer at pH 7.4, at a temperature of about 37 degrees Celsius, and set at rotating speed of 100 rpm. Such methods may be particularly relevant for testing orally dispensable delivery vehicles other than chewing gums, i.e. for example lozenges or fast dissolving tablets. Also, the degree of release or dissolution may be measured as an in vitro release or dissolution, respectfully, carried out on a chewing machine as described herein may e.g. be carried out in accordance with European Pharmacopeia 7 th. ed. 2.9.25 (Chewing gum medicated, drug release from). Such methods may be particularly relevant for testing orally dispensable delivery vehicles such as chewing gums.

Having a desired degree of dissolution may ensure the delivery of cannabinoids to the oral cavity is sufficiently effective, thus promoting the uptake of the one or more cannabinoids from the powdered composition into the body.

The invention further relates to an orally dispensable delivery vehicle comprising the powdered composition of the invention or any of its embodiments.

Thus, it should be understood that when the orally dispensable delivery vehicle is not in the form of a powder, it still comprises the composition of the invention, i.e. said powdered composition. In other words, said powdered composition was used in the making of said orally dispensable delivery vehicle.

In an advantageous embodiment of the invention the orally dispensable delivery vehicle is a tablet for at least partly dissolving in the oral cavity.

Such tablet includes tablets designed to at least partly dissolve in the oral cavity when exposed to an intended use, such as sucking and/or chewing. Said tablet may for example include lozenges, chewing gums, fast dissolving tablets, etc. However, said tablet does not include typical capsules for release in the gastrointestinal tract, which are designed to be swallowed and thereby to bypass the oral cavity without uptake of active ingredients.

In an advantageous embodiment of the invention the orally dispensable delivery vehicle comprises a chewing gum, a lozenge or a fast dissolving tablet.

According to the specific orally dispensable delivery vehicle, further ingredients may be added other than said powdered composition. For example, chewing gums may comprise typical chewing gum ingredients, hereunder gum base, lozenges may comprise typical lozenge ingredients, and fast dissolving tablets may comprise typical ingredients for fast dissolving tablets. The orally dispensable delivery vehicle may also comprise e.g. flavors, sweeteners, hereunder bulk sweeteners and/or high intensity sweeteners.

In an embodiment of the invention the orally dispensable delivery vehicle comprises a chewing gum.

In an embodiment of the invention the orally dispensable delivery vehicle comprises a compressed chewing gum.

In an embodiment of the invention the orally dispensable delivery vehicle comprises a lozenge.

In an embodiment of the invention the orally dispensable delivery vehicle comprises a fast dissolving tablet.

In an embodiment of the invention the orally dispensable delivery vehicle comprises a tablet.

In an advantageous embodiment of the invention the orally dispensable delivery vehicle further comprises acid.

In an advantageous embodiment of the invention the ion exchange resin is a strongly basic ion exchange resin and where the orally dispensable delivery vehicle comprises acid.

One advantage of the above embodiment may be that a desired timely release of the cannabinoid from the complex is obtainable when the orally dispensable delivery vehicle is inserted in the oral cavity while at the same time facilitating a desired flavor or flavor enhancing by means of the citric acid.

In an advantageous embodiment of the invention the orally dispensable delivery vehicle further comprises acid in an amount of between 0.1 and 20 percent by weight of said orally dispensable delivery vehicle.

In an embodiment of the invention the orally dispensable delivery vehicle further comprises acid in an amount of between 0.5 and 10 percent by weight of said orally dispensable delivery vehicle.

In an embodiment of the invention the orally dispensable delivery vehicle further comprises acid in an amount of 1 and 5 percent by weight of said orally dispensable delivery vehicle.

In an advantageous embodiment of the invention the content of cannabinoids in said orally dispensable delivery vehicle is between 1 and 400 milligram.

In an embodiment of the invention the content of cannabinoids in said orally dispensable delivery vehicle is between 1 and 100 milligram.

In an embodiment of the invention the content of cannabinoids in said orally dispensable delivery vehicle is between 2 and 30 milligram.

In an embodiment of the invention the content of cannabinoids in said orally dispensable delivery vehicle is 3 and 25 milligram.

In an embodiment of the invention the content of cannabinoids in said orally dispensable delivery vehicle is between 4 and 20 milligram.

In an embodiment of the invention the content of cannabinoids in said orally dispensable delivery vehicle is between 5 and 15 milligram.

In some other embodiments, the orally dispensable delivery vehicle may comprise a higher amount of cannabinoids, such as between 400 and 1000 milligram of cannabinoids.

In one embodiment, 100 percent of the orally dispensable delivery vehicle, such as a lozenge, is dissolved in the oral cavity in less than about 60 minutes, or in less than about 50 minutes, or in less than about 45 minutes.

The invention further relates to a method of manufacturing the powdered composition of the invention or any of its embodiments, the method comprising the steps of
providing said cannabinoid in a liquid solution,
providing a basic ion exchange resin,
mixing said cannabinoids in liquid solution with said basic ion exchange resin to obtain a mixture,
removing solvent originating from said liquid solution from said mixture.

In some embodiments, the powdered composition may be obtained directly after the step of removing solvent, whereas in other embodiments it may be necessary or desirable to employ further steps, e.g. for obtaining the powdered composition or for e.g. ensuring a certain particle distribution of the obtained powdered composition.

In an advantageous embodiment of the invention at least 50 percent by weight of said solvent is removed.

In an embodiment of the invention at least 75 percent by weight of said solvent liquid solution is removed.

In an embodiment of the invention at least 90 percent by weight of said solvent liquid solution is removed.

In an embodiment of the invention at least 95 percent by weight of said solvent liquid solution is removed.

In an advantageous embodiment of the invention said step of removing solvent comprises exposing said mixture to heat.

In an advantageous embodiment of the invention said step of removing solvent comprises exposing said mixture to pressure lower than atmospheric pressure, for example a pressure of below 500 mbar.

In an embodiment of the invention said step of removing solvent comprises exposing said mixture to pressure below 400 mbar.

In an embodiment of the invention said step of removing solvent comprises exposing said mixture to pressure below 300 mbar.

In an embodiment of the invention said step of removing solvent comprises exposing said mixture to pressure below 200 mbar.

In an advantageous embodiment of the invention said solvent comprises water and/or an alkyl alcohol, such as methanol or ethanol.

In an advantageous embodiment of the invention the method further comprises the step of adding aid substances.

The invention further relates to a method of manufacturing the orally dispensable delivery vehicle of the invention or any of its embodiments, the method comprising the steps of
providing the powdered composition of the invention or any of its embodiments,
adding further ingredients such as bulking agents or fillers,
mixing the powdered composition and the further ingredients, and
forming the orally dispensable delivery vehicle.

The step of forming the orally dispensable delivery vehicle may include pressing, for example when the orally dispensable delivery vehicle is a fast dissolving tablet, a compressed chewing gum, or a lozenge.

The invention further relates to the composition of the invention or any of its embodiments or the orally dispensable delivery vehicle of the invention or any of its embodiments for use as a medicament.

The invention further relates to the composition of the invention or any of its embodiments or the orally dispensable delivery vehicle of the invention or any of its embodiments for use in alleviation of pain, such as neurotic pain or cancer-related pain.

The invention further relates to the composition of the invention or any of its embodiments or the orally dispensable delivery vehicle of the invention or any of its embodiments for use in mitigation of appetite deficiency.

The invention further relates to a method of alleviation of pain, such as neurotic pain or cancer-related pain, by administering an effective amount of the composition of the invention or any of its embodiments or the orally dispensable delivery vehicle of the invention or any of its embodiments.

The invention further relates to a method of mitigation of appetite deficiency by administering an effective amount of the composition of the invention or any of its embodiments or the orally dispensable delivery vehicle of the invention or any of its embodiments.

The invention further relates to use of a basic ion exchange resin as a stabilizing agent in a complex with a cannabinoid comprising at least one phenolic moiety.

In an advantageous embodiment of the invention the cannabinoid complex is provided in the powdered composition of the invention or any of its embodiments or in the orally dispensable delivery vehicle of the invention or any of its embodiments.

DETAILED DESCRIPTION

Some embodiments of the present invention are directed to fast dissolving tablet formulations that can be formed by compression into fast dissolving tablets as an orally dispensable delivery vehicle. The fast dissolving tablets comprise the powdered composition of the invention, which powdered composition comprises a complex between a cannabinoid having at least one phenolic moiety and a basic ion exchange resin. The fast dissolving tablet has at least one compound (or "component") which partially or fully melts or softens at or below body temperature and a water soluble excipient. For example, use of the component which partially or fully melts below body temperature in an amount of about 0.01% to about 2.5% w in the fast dissolving tablet provides for a fast dissolving tablet composition that is conveniently amenable to established tablet manufacturing processes and equipment and to established packaging methods. Amenable to established tablet and manufacturing processes and equipment is taken to mean that the composition (which forms the fast dissolving tablet) may be processed with conventional manufacturing equipment with minimal occurrence of malformed product and/or the need for special equipment maintenance procedures. The low melting point compound may be hydrophilic or hydrophobic. The fast dissolving tablets of the invention may also include further active ingredient(s) and may also include one or more disintegrants, flavors, colorants, sweeteners, souring agents, glidants or lubricants.

The hardness of the fast dissolving tablets is low (less than or equal to about 3 kP), such as less than or equal to about 2 kP, such as less than or equal to about 1 kP, with a minimum hardness of about 0.1 kP (e.g., 0.05, 0.07, 0.1, 0.2, 0.3, 0.4, 0.5, 0.6, 0.7, 0.8, 0.9, 1.0, 1.3, 1.6, 1.9, 2.0, 2.1, 2.3, 2.5, 2.7, 2.8, or 3.0 kP). In embodiments well suited to established manufacturing and packaging methods, the fast dissolving tablet hardness may be for example about 1.2 to about 1.5 kP. In other embodiments, hardness ranges from about 0.2 to about 1 kP. Attributes such as (1) fast stable dissolution; (2) good tablet mouth feel; and (3) good tablet physical stability are of greater importance than minimum and maximum values of tablet hardness. Nevertheless, the fast dissolving tablets are somewhat pliable, and may be less fragile than conventional tablets that have the same crushing strength. The fast dissolving tablets have an excellent mouthfeel resulting from the low melting point component which melts or softens in the mouth to produce a smooth feel and masks the grittiness of insoluble ingredients. The disintegration of the fast dissolving tablets of some embodiment may for example occur by a combination of melting, disintegration of the tablet matrix, and dissolution of water soluble excipient. Disintegration time may in some embodiments be between 10 and 30 seconds (e.g., 10, 12, 14, 16, 18, 20, 22, 24, 26, 28 or 30 seconds), depending on the fast dissolving tablet size and amount of insoluble ingredients. Even though the fast dissolving tablet contains a low melting point ingredient, it may be relatively stable to high temperatures. Heating the fast dissolving tablet above the melting point of its low melting point component will not significantly reduce its physical stability.

Fast dissolving tablets may in some embodiments be made by a method of direct compression at low force.

The friability of conventional tablets is measured by the percentage weight loss after a typical friability test (rotating 10 tablets in a friability apparatus for 100 rotations). This test is very harsh for some fast dissolving tablets and so cannot be used to measure their friability.

Fast dissolving tablets manufactured by the methods in the current invention may in some embodiments withstand 20-50 rotations in the friability apparatus before the fast dissolving tablet breaks. In some embodiments, after 20 rotations, the friability (% weight lost) is typically less than 1%.

The term "low melting point compound" may include any edible compound which melts or softens at or below 37 degrees Celsius which is suitable for inclusion in the fast dissolving tablets of the invention. Materials commonly used for manufacturing suppositories usually have a melting point at or just below body temperature and can be used in the fast dissolving tablets of the invention. The low melting point compound can be hydrophilic or hydrophobic.

Examples of hydrophilic low-melting point compounds include, but are not limited to polyethylene glycol; the mean molecular weight range of polyethylene glycol for use in the fast dissolving tablets of the invention may for example be from about 900 to about 1000. Mixtures of polyethylene glycol with different molecular weights (200, 300, 400, 550, 600, 1450, 3330, 8000 or 10,000) are within the scope of the invention if the mixture melts or softens at or below 37 degrees Celsius.

Examples of hydrophobic low-melting point compounds include, but are not limited to, low melting point triglycerides, monoglycerides and diglycerides, semisynthetic glyceride (e.g., EUTECOL®, GELUCIRE® (Gattefosse)), hydrogenated oils, hydrogenated oil derivatives or partially hydrogenated oils (e.g. partially hydrogenated palm kernel oil and partially hydrogenated cottonseed oil), fatty acid esters such as myistyl lactate, stearic acid and palmitic acid esters, cocoa butter or its artificial substitutes, palm oil/palm oil butter, and waxes or mixtures of waxes, which melt at 37 degrees Celsius or below. In some embodiments, the hydrogenated oil is Wecobec M. To be effective in the fast dissolving tablet compositions, the low melting point compound must be edible.

Mono-, di- and triglycerides may in some embodiments be used as pure components. Hydrogenated vegetable oils and solid or semisolid fats are usually mixtures of mono-, di- and triglycerides. The melting point of the fat or hydrogenated vegetable oil is characteristic of the mixture and not due to a single component Witepsol (brand name by Condea), Supocire (brand name by Gattefosse), and Novata (brand name by Henkel) are commonly used in manufacturing suppositories, because they melt a body temperature. All are mixtures of triglycerides, monoglycerides and diglycerides.

In some embodiments, the low melting point compound comprises from about 0.01 percent by weight to about 20 percent by weight, of a fast dissolving tablet composition (e.g. about 0.01, 0.1, 1, 2.5, 5. 7.5, 10, 12, 14, 15, 16, 18 or 20 percent by weight). Concentration of low melting point compound in the amount of about 0.01 percent by weight to about 2 percent by weight of the fast dissolving tablet may for example be when established manufacturing and packaging methods are used. The fast dissolving tablets of the present invention also include a water soluble excipient. As used herein, the term "water soluble excipient" refers to a solid material or mixture of materials that is orally ingestible and readily dissolves in water. Examples of water soluble excipients include but are not limited to saccharides, amino acids, and the like. Saccharides is one well-suited water soluble excipient. For example, the saccharide is a mono-, di- or oligosaccharide. Examples of saccharides which may be added to the fast dissolving tablets of the invention may include sorbitol, glucose, dextrose, fructose, maltose and xylitol (all monosaccharides); sucrose, lactose, glucose, galatose and mannitol (all disaccharides). In one embodiment, exemplified below, the saccharide is lactose. In one embodiment, the saccharide is mannitol. Other suitable saccharides are oligosaccharides. Examples of oligosaccharides include dextrates and maltodextrins. Modified saccharides such as sucralose or other artificial sweeteners such as saccharin or aspartame, for example, may also be used. Other water soluble excipients may for example include amino acids such as alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine. Glycine and lysine are examples of well-suited amino acids.

In some embodiments, the water soluble excipient comprises from about 25 to about 97.5 percent by weight of a fast dissolving tablet composition. The range may for example be about 40 to about 80 percent by weight. For example, fast dissolving tablet compositions comprising about 25, 30, 35, 40, 45, 50, 55, 60, 65, 70, 75, 80, 85, 90, 95 or 97.5 percent by weight of the excipient, e.g. monosaccharide, disaccharide, polysaccharide, modified saccharide, artificial sweetener or mixtures thereof are within the scope of the invention.

Fast dissolving tablet shapes may for example be cylindrical, spherical, rectangular, capsular or irregular. The term "fast dissolving tablet composition" refers to the substances included in a fast dissolving tablet. A "fast dissolving tablet composition constituent" or "fast dissolving tablet constituent" refers to a compound or substance which is included in a fast dissolving tablet composition. These can include, but are not limited to the complex comprising cannabinoid(s) and any excipients in addition to the low melting point compound and the water soluble excipient(s). An excipient is any ingredient in the fast dissolving tablet except the cannabinoid(s). In addition to the low melting point compound excipients may include, for example, binders, disintegrants, flavorants, colorants, glidants, souring agents and sweeteners.

For purposes of the embodiments relating to fast dissolving tablets, "binder" refers to one or more ingredients added before or during granulation to form granules and/or promote cohesive compacts during compression. A "binder compound" or "binder constituent" is a compound or substance which is included in the binder. Binders of the present invention include, at least, the low melting point compound.

Additionally, and optionally, other substances commonly used in pharmaceutical formulations can be included such as flavors (e.g., strawberry aroma, raspberry aroma, cherry flavor, magnasweet 135, key lime flavor, grape flavor trusil art 5-11815, fruit extracts and prosweet), flavor enhancers and sweeteners (e.g. aspartame, sodium saccharine, sorbitol, glucose, sucrose), souring agents (e.g. citric acid), dyes or colorants.

The fast dissolving tablet may also contain one or more glidant materials which may improve the flow of the powder blend and minimize fast dissolving tablet weight variation. Glidants such as silicone dioxide may be used in the fast dissolving tablets of the present invention.

Additionally, the fast dissolving tablets of the invention may include lubricants (e.g. magnesium stearate) to facilitate ejection of the finished fast dissolving tablet from dies after compression and to prevent fast dissolving tablets from sticking to punch faces and each other.

Any method of forming a fast dissolving tablet of the invention into a desired shape which preserves the essential features thereof is within the scope of the invention.

In some embodiments, the method of forming the fast dissolving tablet compositions includes preparing a fast dissolving granulation by mixing a low-melting point compound, (for example a hydrogenated oil, partially hydrogenated oil or hydrogenated oil derivative) and a water soluble excipient, (for example a saccharide or modified saccharide). The term "fast dissolving granulation" refers to a composition of the low melting point compound and the water soluble excipient prepared for use as a granulation in the manufacture of fast dissolving tablets of the invention. A portion of the fast dissolving granulation may then be added to the remaining ingredients. However, methods of forming the fast dissolving tablets of the invention wherein all fast dissolving tablet constituents are combined simultaneously or wherein any combination of fast dissolving tablet constituents are combined separate from the other constituents are within the scope of the invention.

Granulation end point can be determined visually (visual inspection) or by using a load cell that measures power consumption. Tablet manufacturing and granulation routinely employ both techniques.

The fast dissolving tablet compositions of the invention can be formed by melt granulation which is a suitable method. In particular, the melt granulation can be prepared in a high shear mixer (e.g. high sheer granulation process), low sheer mixer or fluid bed granulator. An example of high shear mixer is Diosna (this is a brand name by Diosna Dierks & Sohne GmbH). Examples of low shear mixers are various tumbling mixers (e.g. twin shell blenders or V-blender). Examples of fluid bed granulators are Glatt and Aeromatic fluid bed granulators.

Examples of manufacturing the granulation include, but are not limited to:

Melting the low melting point ingredient, then combining (e.g. by spraying) it with the water soluble ingredient(s) (including the water soluble excipient) in the granulator and mixing until granules form.

Loading the water soluble excipient in the granulator and spraying the molten low melting point compound on it while mixing.

Combining the two (water soluble component (including the water soluble excipient) and low melting point component) and possibly other ingredients and mixing while heating to a temperature around a higher than the melting point of the low melting point component until the granules form.

After the granulation congeals, it may be milled and/or screened. Examples of mills that can be used are Co Mill. Stokes Oscillator (these are brand names). Any mills that are commonly used for milling tablet granulations may be used.

Melt extrusion can be used to form the fast dissolving granulation. An example of an extruder that can be used is Nica (a brand name by Niro-Aeromatic). The low melting point compound and the water soluble saccharide (or other excipient) are mixed and heated in a planetary mixer bowl (low shear mixer) that is usually part of the extruder. The soft mass is then fed to the extrusion chamber and forced through small holes or orifices to shape it into thin rods or cylinders. After the extruded material congeals it can be milled or spheronized using standard equipment. In the spheronization step, the extrudate is dumped onto the spinning plate of the spheronizer and broken up into small cylinders with a length equal to their diameter, then rounded by frictional forces (See, International Journal of Pharmaceutics 1995, 116:131-146, especially p. 136).

Spray congealing or prilling can also be used to form the fast dissolving tablet compositions of the invention. Spray congealing includes atomizing molten droplets of compositions which, may include low melting point compound, low melting point compound and selected fast dissolving tablet ingredients, or the entire fast dissolving tablet composition onto a surface. The surface may be an inert mechanical support, a carrier surface or in embodiments in which the spray contain droplets only part of the fast dissolving tablet components a second portion of the fast dissolving tablet composition. Equipment that can be used for spray congealing includes spray driers (e.g., Nero spray drier) and a fluid bed coater/granulation with top spray (e.g., Glatt fluid bed coater/granulator). In some embodiments, a fast-dissolve granulation is formed wherein e.g. a water soluble excipient, such as a saccharide, is suspended in a molten low melting point ingredient and spray congealed. After spray congealing, the resulting composition is allowed to cool and congeal. Following congealing of the mixture, it is screened or sieved and mixed with remaining fast dissolving tablet constituents. Spray congealing processes wherein fast-dissolve granulations comprising any combination of low melting point compound and other fast dissolving tablet constituents are melted and spray congealed onto other fast dissolving tablet constituents are within the scope of the present invention. Spray congealing processes wherein all fast dissolving tablet constituents, including the low-melting point compound, are mixed, the low melting point compound is melted and the mixture is spray congealed onto a surface are also within the scope of the invention.

After spray congealing, the mixture may be milled and then combined with other fast dissolving tablet constituents. Following formation of the final fast dissolving tablet composition, the composition may be further processed to form a fast dissolving tablet shape.

Mixing and milling of fast dissolving tablet constituents during the preparation of a fast dissolving tablet composition may be accomplished by any method which causes the composition to become mixed to be essentially homogeneous. In some embodiments the mixers are high shear mixers such as the Diosna, CoMill or V-B lender.

Once fast dissolving tablet compositions are prepared, they may be formed into various shapes. In some embodiments, the fast dissolving tablet compositions are pressed into a shape. This process may comprise placing the fast dissolving tablet composition into a form and applying pressure to the composition so as to cause the composition to assume the shape of the surface of the form with which the composition is in contact. In some embodiments, the fast dissolving tablet is compressed into the form at a pressure which will not exceed about 10 kN, such as less than 8 kN. For example, pressing the fast dissolving tablets at less than 1, 1, 1.5, 2, 2.5, 3, 3.5, 4, 4.5, 5, 6, 7, 8, 9 or 10 kN is within the scope of the invention. The fast dissolving tablets of the invention generally have a hardness of about 3 kP or less; such as a hardness of about 2 kP or less, such as about 1 kP or less. Fast dissolving tablet compositions subjected to established manufacturing methods may have a hardness of about 1 to about 2.0, such as a hardness of about 1.2 to about 1.5. In another embodiment, for example, fast dissolving tablets of less than 0.1 kP including fast dissolving tablets of about 0.05, 0.07 kP and fast dissolving tablets of about 0.2, 0.3, 0.4, 0.5, 0.6, 0.7, 0.8, 0.9, 1.0, 1.3, 1.6, 1.9, 2.0, 2.1, 2.3, 2.5, 2.7, 2.8, or 3.0 are within the scope of the invention. Hydraulic presses such as a Carver Press or rotary tablet presses such as the Stokes Versa Press are suitable means by which to compress the fast dissolving tablet compositions of the invention.

Fast dissolving tablets may also be formed by tumbling melt granulation (TMG) essentially as described in Maejima et al. Chemical Pharmacology Bulletin (1997) 45(3): 518-524; which is incorporated herein by reference. Tumbling melt granulation can be used for preparing the melt granulation. It can be done in a tumbling mixer. The molten low melting point compound is sprayed on the crystalline saccharide and powdered saccharide in the blender and are mixed until granules form. In this case, the low melting point ingredient is the binder and the crystalline saccharide is the seed. An alternative method is to combine the unmelted low melting point ingredient, crystalline sugar (e.g., mannitol or lactose) in the tumbling mixer and mix while heating to the melting point of the low melting point binder or higher. The seed should be crystalline or granular water soluble ingredient (saccharide), e.g., granular mannitol, crystalline maltose, crystalline sucrose, or any other sugar. An example of tumbling mixers is the twin-shell blender (V-blender), or any other shape of tumbling mixers. Heating may for example be achieved by circulating heated air through the chamber of the granulator and by beating the bottom surface of the chamber. As the seed material and the powdered fast dissolving tablet constituents circulate the heated chamber, the low-melting point compound melts and adheres to the seeds. The unmelted, powdered material adheres to the seed-bound, molten low-melting point material. The spherical beads which are formed by this process are then cooled and screen sifted to remove nonadhered powdered material.

Some embodiments of the present invention are directed to a lozenge as an orally dispensable delivery vehicle. The lozenges comprise the powdered composition of the invention, which powdered composition comprises a complex between a cannabinoid having at least one phenolic moiety and a basic ion exchange resin. The lozenges comprise further ingredients. In some embodiments, such further ingredients may include a combination of water soluble synthetic or semi-synthetic non-ionic polymers having varied viscosities.

As used herein, water soluble synthetic or semisynthetic non-ionic polymers may include, but are not limited to alkylcelluloses, hydroxyalkylcelluloses, hydroxyalkyl alkylcelluloses, polyalkylene oxides, carboxyalkylcellulose esters methacrylate copolymers; polyvinylalcohol; polyvinylpyrrolidone, copolymers of polyvinylpyrrolidone with vinyl acetate; combinations of polyvinylalcohol and polyvinylpyrrolidone and copolymers of ethylene oxide and propylene oxide.

Examples of alkylcelluloses may include methylcellulose. Examples of hydroxyalkylcelluloses may include hydroxymethylcellulose, hydroxyethylcellulose, hydroxypropylcellulose and hydroxybutylcellulose. Examples of hydroxyalkyl alkylcelluloses may include hydroxyethyl methylcellulose and hydroxypropyl methylcellulose. Examples of polyalkylene oxides may include polyethylene oxide and polypropylene oxide. Water soluble synthetic or semisynthetic non-ionic polymers may also include dextrin, semisynthetic starch, polyhydroxyethylmethacrylate (PHEMA), water soluble nonionic polymethacrylates and their copolymers, modified cellulose, modified polysaccharides, nonionic semisynthetic gums, nonionic polysaccharides and/or mixtures thereof.

In certain embodiments, the polymer is a cellulose ether derivative such as hydroxypropyl methylcellulose and hydroxypropyl cellulose. In another embodiment, the polymer is hydroxypropyl methylcellulose. In yet another embodiment, the polymer is hydroxypropylmethyl cellulose (HPCM). In certain embodiments, the polymer has an average particle size range of between about 10 and about 100 1.un, or between about 20 and about 80 ~m, or between about 40 and about 60 ~m.

Lozenges of the some embodiments may for example contain a polymer having a high viscosity and a polymer having a low viscosity. In certain embodiments, the polymer having the high viscosity has a viscosity of from about 2,000 cps to about 6,000 cps, or from about 3,000 cps to about 5,000 cps, or from about 3,500 cps to about 5,500 cps. In one embodiment, the high viscosity polymer has a viscosity of about 4,000 cps. Viscosity for the high viscosity polymers was determined using a Brookfield type LV Model, or equivalent.

In certain embodiments, the polymer having the low viscosity has a viscosity of from about 50 cps to about 150 cps, or from about 80 cps to about 100 cps, or from about 90 cps to about 110 cps. In one embodiment, the low viscosity polymer has a viscosity of about 100 cps. Viscosity for the low viscosity polymers was determined using Capillary Viscometer Methods 911.

The amount of high viscosity polymer may be from between about 1% to about 20% by weight, or from between about 2% to about 10% by weight, or from about 3% to about 7% by weight. The amount of low viscosity polymer may be from between about 1% to about 20% by weight, or from between about 2% to about 10% by weight, or from about 3% to about 7% by weight.

The ratio of high viscosity polymer to low viscosity polymer in the lozenge may vary depending upon the desired dissolution characteristics of the lozenge. For example, if a slowly dissolving lozenge is desired, a higher ratio of high viscosity polymer to low viscosity polymer may be desired. If, however, a quickly dissolving lozenge is desired, a lower ratio of high viscosity polymer to low viscosity polymer may be desired. In certain embodiments, the ratio of high viscosity polymer to low viscosity polymer may be between about 1:50 and about 50:1, or between about 1:30 and about 30:1, or between about 1:20 and about 20:1, or between about 1:10 and about 10:1, or between about 1:2 and about 2:1.

In some embodiments optimization of the ratio of high viscosity polymer to low viscosity polymer may result in a lozenge with improved dissolution characteristics. For example, too much high viscosity polymer may result in lozenges having highly varied dissolution profiles on a lozenge to lozenge basis. In addition, the amount of high viscosity polymer may not be consistent on an intra-lozenge basis—i.e., the high viscosity polymer may not be evenly distributed throughout the lozenge. If only low viscosity polymers are used in a lozenge, the cannabinoid(s) may be released from the lozenge too quickly. To obtain an appropriate release using only low viscosity polymer, a large amount of polymer may be required, resulting in a larger lozenge tablet, which may be regarded as having undesirable textural properties, e.g. that the lozenge tablet may have a slimy mouth feel.

According to some embodiments of the invention, a combination of high viscosity polymer and low viscosity polymer are used in the lozenge. In some embodiments, this may result in lozenge to lozenge dissolution variation being well controlled.

Lozenges of the present invention may in some embodiments also include at least one diluent, at least one excipient selected from the group consisting of taste masking agents, antioxidants, glidants, and colorants, or any combination thereof.

Suitable diluents for lozenges of the invention or embodiments thereof may include, for example, maltitol, maltose, fructose, glucose, trehalose, sorbitol, sucrose, sugar, mannitol, xylitol, isomalt, dextrose, maltodextrin, dextrates, dextrin, erythritol, lactitol, polydextrose and mixtures thereof. In one embodiment, the diluent is mannitol. In one embodiment, the diluent is present from about 500 mg to about 1100 mg per lozenge, in another embodiment from about 750 mg to about 1000 mg per lozenge.

Suitable taste masking agents for lozenges of the invention or embodiments thereof may include, but are not limited to intensive sweetening agents and/or flavorants. Suitable intensive sweetening agents for lozenges of the invention or embodiments thereof may include, but are not limited to, aspartame, acesulfame K, cyclamate and salts thereof, glycyrrhizin and salts thereof, neohesperidine, sucralose, saccharin and salts thereof, thaumatin and mixtures thereof. Suitable flavorants for lozenges of the invention or embodiments thereof may include, but are not limited to, menthol, peppermint, wintergreen, sweet mint, spearmint, vanillin, chocolate, coffee, cinnamon, clove, tobacco, citrus and fruit flavors and mixtures thereof. When present, taste masking agents may for example be present in an amount from about 1 mg to about 50 mg per lozenge, or from about 10 mg to about 20 mg per lozenge.

Suitable antioxidants for lozenges of the invention or embodiments thereof may include, but are not limited to sodium benzoate, butyl-hydroxy toluene and tocopherol and its salts. Suitable glidants for lozenges of the invention or embodiments thereof may include, but are not limited to, talc, corn starch, stearic acid, calcium stearate, polyethylene glycol, colloidal silicon dioxide, sodium stearyl fumarate, magnesium stearate, vegetable and mineral oils and mixtures thereof. In one embodiment the glidant is magnesium stearate. Suitable colorants for lozenges of the invention or embodiments thereof may for use herein include any pigments, dyes, lakes or natural food colors that are suitable for food and drug applications, e.g. FD&C dyes and lakes.

Lozenges of the present invention or embodiments thereof may have a total weight per lozenge of between about 100 mg and about 2000 mg, or between about 500 mg and about 1500 mg. or between about 1000 mg and about 1300 mg. In one embodiment the total weight per lozenge is about 1200 mg.

Lozenges of the present invention or embodiments thereof may be compressed by traditional tableting compression techniques. In certain embodiments, the lozenges may be compressed to a hardness of from about 20 N to about 200 N, or from about 30 N to about 150 N, or from about 50 N to about 100 N.

Certain embodiments of the present invention are directed to lozenges comprising an intragranular component and an extragranular component. The use of intragranular components for formulations is common in solid dosage forms such as tablets and compressed lozenges. Typically, the intragranular component (or "master granules") is made to improve the processability of a solid dosage form and to reducing friability during transportation and handling. In the absence of an intragranular component. tablets or lozenges where high levels of non-direct compressible diluents are used can be difficult to process or result in a product with high friability. Cannabinoid(s), and other optional excipients and flavoring agents, may for example be blended with the intragranular component, prior to compressing, and make up the "extragranular" component of these traditional lozenge formulations. Alternatively, the cannabinoid(s) may be included in the intragranular components.

Intragranular components may in some embodiments be formed by suitable means such as, for example, slugging, aqueous or non-aqueous wet granulation, fluidized bed granulation, spray drying or roller compaction. In one embodiment, the granulate is formed by a wet granulation process, wherein the intragranular ingredients are mixed in a suitable granulator to form a powder blend. Water or a suitable solvent or solvent mixture may be added and mixed thoroughly with the powder blend. This process may allow the powder blend to become wet and to agglomerate to form granules. The wet granulate may then be dried, e.g. in a conventional tray drier, and then generally milled and screened to obtain granules with a desired particle size distribution. In another example embodiment, the granulate is formed by a fluidized bed granulation process in which the intragranular ingredients are fluidized in a fluid bed drier and then sprayed with water or suitable solvent. The wet granules so formed are dried and are then generally milled and screened to obtain granules with a desired particle size distribution. In another example embodiment spray granulation is used as a method to granulate powders to obtain spherical free flowing granules. In a spray granulation operation, the desired intragranular ingredients may be suspended in water or suitable solvent. This suspension is sprayed using an atomizer into a spray drier. The droplets so generated by the atomizer may then be dried to form granules, which are then generally milled and screened to obtain granules with a desired particle size distribution. In yet another example embodiment, roller compaction may be used as a method for manufacture of the granulate, where a dry blend of the other desired intra granular ingredients are forced through a pair of rollers held under high pressure, thereby compacting the powder compacts to form wafer like sheets, which may then be generally milled and screened to obtain granules with a desired particle size distribution. Small amounts of water can be sprayed on to the powder blend prior to feeding in to the rollers to enhance the binding properties of the ingredients in this process. The granules so obtained by any of the granulation processes described can be further processed to obtain tablets or lozenges.

Presence of polymer in the intra granular component and extragranular component may serve two separate functions. Polymer in the intragranular component may serve as a binder to form the master granules. The intragranular component may in some embodiments include a high viscosity water soluble synthetic or semi-synthetic non-ionic polymer, a low viscosity water soluble synthetic or semi-synthetic non-ionic polymer, or both. In one embodiment, the intragranular component contains both a high viscosity water soluble synthetic or semisynthetic non-ionic polymer and a low viscosity water soluble synthetic or semi-synthetic non-ionic polymer. The amount of high viscosity water soluble synthetic or semi-synthetic non-ionic polymer may be from between about 1% and about 20% by weight, or from between about 2% and about 10% by weight, or from about 3% and about 7% by weight. The amount of low viscosity water soluble synthetic or semisynthetic non-ionic polymer may in some embodiments be from between about 1% to about 20% by weight, or from between about 2% to about 10% by weight, or from about 3% to about 7% by weight. In one embodiment, the intragranular component comprises about 5% high viscosity water soluble synthetic or semi-synthetic non-ionic polymer and about 5% low viscosity water soluble synthetic or semi-synthetic non-ionic polymer.

In some embodiments, the ratio of high viscosity water soluble synthetic or semi-synthetic non-ionic polymer to low viscosity water soluble synthetic or semi-synthetic non-ionic polymers in the intragranular component may be between about 1:50 and about 50:1, or between about 1:30 and about 30:1, or between about 1:20 and about 20:1, or between about 1:10 and about 10:1, or between about 1:2 and about 2:1.

Presence of polymer in the extragranular component may in some embodiments act as a dissolution modifier. Various dissolution profiles can be achieved by varying the amount and ratios of high viscosity polymer and low viscosity polymers. The extragranular component may in some embodiments include a high viscosity water soluble synthetic or semi-synthetic non-ionic polymer, a low viscosity water soluble synthetic or semi-synthetic non-ionic polymer, or both. In one embodiment, the extra granular component includes a low viscosity water soluble synthetic or semi-synthetic non-ionic polymer.

The amount of high viscosity water soluble synthetic or semi-synthetic non-ionic polymer may in some embodiments be between about 1% and about 20% by weight, or between about 2% and about 10% by weight, or between about 3% and about 7% by weight. The amount of low viscosity water soluble synthetic or semi-synthetic non-ionic polymer may in some embodiments be between about 1% and about 20% by weight, or between about 2% and about 10% by weight, or between about 3% and about 7% by weight.

In one embodiment, the extragranular component contains about 2% low viscosity water soluble synthetic or semi-synthetic non-ionic polymer, or about 5% low viscosity water soluble synthetic or semi-synthetic non-ionic polymer, or about 18% low viscosity water soluble synthetic or semisynthetic non-ionic polymer.

The ratio of high viscosity water soluble synthetic or semi-synthetic non-ionic polymer to low viscosity water soluble synthetic or semi-synthetic non-ionic polymer in the intra granular component may in some embodiments be between about 1:50 and about 50:1, or between about 1:30 and about 30:1, or between about 1:20 and about 20:1, or between about 1:10 and about 10:1, or between about 1:2 and about 2:1.

Cannabinoid(s) may according to various embodiments be present in the intragranular component, the extragranular component or both. In one embodiment, cannabinoid(s) is/are present in the extragranular component. A pH controlling acid may also be present in the intragranular component, the extragranular component or both. In one embodiment, a pH controlling acid is present in the extragranular component. In another embodiment, a pH controlling acid is present in the intra granular component and the extra granular component.

Lozenges of the present invention may have an in vitro dissolution profile (as determined by USP Type II apparatus, rotating paddle, with 900 ml of Phosphate buffer at pH 7.4, 37° C. set at rotating speed of 75 rpm) of: 25 to 50% at 1 hour; 50 to 99% at 3 hours; 75 to 100% at 6 hours.

In other embodiments, lozenges of the present invention may have an in vitro dissolution profile (as determined by USP Type II apparatus, rotating paddle, with 900 ml of Phosphate buffer at pH 7.4, 37° C. set at rotating speed of 75 rpm) of: 30 to 40% at 1 hour; 50 to 70% at 3 hours; 90 to 100% at 6 hours.

In yet other embodiments, lozenges of the present invention may have an in vitro dissolution profile (as determined by USP Type I apparatus, basket, Phosphate buffer at pH 7.4, 37° C. set at rotating speed of 100 rpm) of: 33 to 37% at 1 hour; 65 to 70% at 3 hours; 97 to 100% at 6 hours.

In certain embodiments, lozenges of the present invention may have the following dissolution profile in the oral cavity: 45 to 60% at 15 minutes; 70 to 85% at 30 minutes; 90 to 100% at 60 minutes.

In another embodiment, lozenges of the present invention may have the following dissolution profile in the oral cavity: 50 to 55% at 15 minutes; 75 to 80% at 30 minutes; 95 to 100% at 60 minutes.

In one embodiment, 100% of a lozenge of the present invention is dissolved in the oral cavity in less than about 60 minutes, or in less than about 50 minutes, or in less than about 45 minutes.

In another embodiment, at least about 50% of the lozenge is dissolved in the oral cavity in less than about 30 minutes or in less than about 15 minutes.

Some embodiments of the present invention are directed to chewing gums, such as compressed chewing gums, as an orally dispensable delivery vehicle. The chewing gums comprise the powdered composition of the invention, which powdered composition comprises a complex between a cannabinoid having at least one phenolic moiety and a basic ion exchange resin. The chewing gums also comprises gum base, and may comprise further ingredients.

The term "powdered portion of chewing gum tablet base material" is intended to mean a portion of discrete particles of chewing gum tablet base material.

The term "base material" is intended to mean a material that forms the basis of the material, usually constituting a major part of the material.

The term "gum base", "gum base matrix" or "gum base portion" is intended to mean the mainly water insoluble and hydrophobic gum base ingredients that are mixed together before the bulk portion of the chewing gum composition is added.

The term "bulk portion" intends to mean the mainly water soluble and hydrophilic chewing gum ingredients that are mixed into the gum base matrix after the gum base matrix has been prepared.

By the phrase "chewing gum" is meant any chewing gum such as extruded chewing gum, centre-filled chewing gum, toffee-imitating chewing gum, compressed chewing gum, slabs or sticks.

By the phrase "granules of gum base" is meant granules consisting of gum base.

By the phrase "granules of chewing gum" is meant granules consisting of granulated chewing gum, wherein said chewing gum comprises gum base.

By the phrase "compressed chewing gum" is meant a chewing gum comprising granules or powder being exposed to a punching means in a tableting machine, pressing the granules or powder to a coherent mass of compressed material.

By the phrase "texture" is meant a qualitative measure of the visco-elastic properties the chewing gum and of the overall mouth-feel experienced by the user during the chewing process. Thus the term "texture" encompasses measurable quantities such as hardness and elasticity as well as more subjective parameters related to the chew-feel experienced by a user.

The phrase "hydrophobic" is used to describe the ability of a substance to dissolve in or blend with apolar substances such as e.g. oils.

The phrase "hydrophilic" is used to describe the ability of a substance to dissolve in or blend with polar substances, such as e.g. water.

In some embodiments of the present invention, the gum base comprises for example
  elastomer in the range of 5-40% by weight of the gum base,
  natural resin in the range of 8-45% by weight of the gum base, and
  synthetic resin in the range of 5-95% by weight of the gum base.

In some embodiments of the present invention, the chewing gum tablet comprises natural resins in an amount of 0.1 to 40%, such as 1 to 30%, such as 3 to 25% or 5 to 20%, by weight of the chewing gum tablet.

In some embodiments of the present invention, the chewing gum tablet comprises natural resins in an amount of at least 13% by weight of the chewing gum tablet.

In embodiments of the present invention, the chewing gum tablet comprises synthetic resins in an amount of 0.1 to 40%, such as 1 to 30%, such as 3 to 25% or 5 to 20%, by weight of the chewing gum tablet.

In embodiments of the present invention, the chewing gum tablet comprises elastomer in an amount of at least 2% by weight of the chewing gum formulation, such as at least 4% by weight of the chewing gum tablet.

In embodiments of the present invention, the chewing gum tablet comprises elastomer in an amount of less than 35% by weight of the chewing gum formulation, such as less than about 25% by weight of the chewing gum formulation such as less than 20%, 15% or 10% by weight of the chewing gum tablet.

In embodiments of the present invention, the chewing gum tablet comprises one or more flavoring agents selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, eucalyptus, mint, or any combination thereof.

In embodiments of the present invention, the chewing gum tablet comprises humectants, such as propylene glycol or glycerol.

In embodiments of the present invention, the chewing gum tablet is provided with a coating.

In embodiments of the present invention, the chewing gum tablet has a weight in the range of 0.1 to 10 grams, such as in the range of 0.5 to 4 grams.

According to an embodiment of the invention, the chewing gum tablet may comprise filler. In embodiments of the present invention, the chewing gum tablet comprises filler in an amount of 0.1 to 50% by weight of the chewing gum. In embodiments of the present invention, the chewing gum tablet comprises filler in an amount of 0.1 to 50% by weight of the chewing gum tablet, wherein the filler is hydrophobic and wherein at least 90% of the filler is contained in the chewing gum tablet throughout the chewing of a user during a chewing period of at least 10 minutes.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkane chains of the waxes.

The elastomers (rubbers) employed in the gum base may vary depending upon various factors such as the type of gum base desired, the texture of gum formulation desired and the other components used in the formulation to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base formulations include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

Natural resins may be used according to the invention and may be natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

In an embodiment of the invention, the powdered chewing gum tablet base materials are selected from the group consisting of bulk sweeteners, flavors, dry-binders, tabletting aids, anti-caking agents, emulsifiers, antioxidants, enhancers, absorption enhancers, high intensity sweeteners, softeners, colors, or any combination thereof.

In an embodiment of the invention, the powdered chewing gum tablet base material comprises sweeteners, such as bulk sweeteners, sugar sweeteners, sugar substitute sweeteners, artificial sweeteners, high-intensity sweeteners, or any combination thereof.

Suitable bulk sweeteners include both sugar and non-sugar sweetening components. Bulk sweeteners typically constitute from about 5 to about 95% by weight of the chewing gum tablet, more typically about 20 to about 80% by weight such as 30 to 70% or 30 to 60% by weight of the chewing gum tablet.

Useful sugar sweeteners are saccharide-containing components commonly known in the tablet and chewing gum tablet art including, but not limited to, sucrose, dextrose, maltose, dextrins, trehalose, D-tagatose, dried invert sugar, fructose, levulose, galactose, corn syrup solids, and the like, alone or in combination.

As an example, sorbitol can be used as a non-sugar sweetener. Other useful non-sugar sweeteners include, but are not limited to, other sugar alcohols such as mannitol, xylitol, hydrogenated starch hydrolysates, maltitol, isomalt, erythritol, lactitol and the like, alone or in combination.

High intensity artificial sweetening agents can also be used alone or in combination with the above sweeteners. For example, high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (such as from about 0.02 to about 8% by weight). When carriers used for encapsulation are included, the usage level of the encapsulated sweetener will be proportionately higher. Combinations of sugar and/or non-sugar sweeteners may be used in the chewing gum formulation.

A chewing gum tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

A number of chewing gum tablet base materials well known within the art may be applied within the scope of the present invention. Such components comprise but are not limited to waxes, fats, softeners, fillers, flavors, anti-oxidants, emulsifiers, colouring agents, binding agents and acidulants In an embodiment of the invention, the chewing gum tablet is provided with an outer coating.

In an embodiment of the invention, said outer coating is selected from the group consisting of hard coating, soft coating and edible film-coating or any combination thereof.

The gum base granules according to the invention may for example be made by means of extrusion and under-water pelletizing.

The size of gum base granules according to the present invention are controlled by several factors such as opening sizes, the gum composition, gum temperature and pressure drop, if a die plate is used in the extruder. Due to an interaction between the pressurized gum composition, temperature and friction in the openings of the die device, the average diameter of the produced granules are normally larger than the diameters of the openings in the die device. The relation between the diameters of the openings in the die device and the average diameters of granules produced from a specific gum composition may be determined by the skilled person on basis of routine experiments.

According to the invention it is also possible to produce granules with different average diameters by making granules with one diameter, and subsequently mix the granules with different average diameters in desired proportions.

Although the openings of the die device may have cross-sections of any desired shape, e.g. circular, oval, square etc., it is in some embodiments preferred that the die device comprises openings with substantially circular cross-section and diameters in the range of 0.1 to 1.3 mm. A first set of openings can e.g. have a first diameter in the range of 0.07 to 0.7 mm, such as in the range of 0.15 to 0.6 mm, and suitably in the range of 0.2 to 0.5 mm. A second set of openings can have a second diameter larger than said first diameter. The second diameter is conveniently in the range of 0.4 to 1.3 mm, such as in the range of 0.7 to 1.2 mm.

In some embodiments the chewing gum granulating system further comprises a drying device. Powder sweetener or talk may be added to the granules in a final drying step. The drying device can be a conventional centrifugal dryer or another suitable dryer e.g. a fluid bed dryer. The drying device can, for example, include a mixer. The powder sweetener may in an embodiment be sorbitol, which is mixed to the dried or partially dried granules. Minor amounts of residual moisture on the surface of the granules, e.g. 2% Wt. based on the total weight of the granules, may contribute to the adherence of the sorbitol powder to the surface of the granules. It is possible to use a conventional anti-agglomerating agent as e.g. talcum, but sorbitol powder can function as an anti-agglomerating agent, and at the same time serves as sweetener. Although sorbitol is found to be most suitable, other bulk sweeteners based on polyols may also be suitable, e.g. mannitol, xylitol, hexa-resorcinol, maltitol, isomalt, erythriol, and lactitol.

In one embodiment the chewing gum granulating system according to the invention further comprises one or more sieves adapted for removing granules with an average diameter such as above 1.3 mm. The removal of larger granules improves a subsequent tabletting process.

According to an embodiment of the invention at least the extruder and/or the die device comprises means for controlling the temperature of the chewing gum composition. The means for controlling temperature can be cooling or heating devices, and may serve to facilitate the flow of gum composition through the extruder and the die device. In an embodiment the extruder comprises delivering means for delivering sweetener and/or flavour to the gum composition in the extruder.

During extrusion of the gum composition the differential pressure between the gum composition in the extruder and the gum composition in the liquid filled chamber, i.e. over the die device is suitably above 10 bar, such as above 18 bar, such as in the range of 25 to 90 bar. The temperature of the gum composition in the extruder may for example be in the range of 40 to 125° C., suitably in the range 50 to 115° C. The temperature of the die device may for example be in the range of 60 to 250° C., suitably in the range 80 to 180° C. The temperature of the liquid in the liquid filled chamber is conveniently in the range of 8 to 40° C. The optimum for the pressures and temperatures in the method according to the invention may, however, may be determined by the skilled person as a matter of routine. The optimum values for specific gum compositions, varies of course, depending on the composition.

The quick cooling in the air filled or water-filled chamber may act to preserve possible fragile ingredients in the gum composition so that their qualities are better kept intact and conveyed into the granules included in the final gum product. This improved quality of the gum composition in the granules improves the general composition of the chewing gum product.

Granule fractions of different average weights may be produced with two different setups, each producing a batch of granules of a particular average weight, followed by a blending of the fractions. It is also possible to design a die means with die openings of at least two different sizes to simultaneously obtain granules with different average diameter. Thus it is possible to obtain granules having different weights. More than two different average weights may be obtained, depending on the design of the die means in use. It is for instance possible to obtain granules with three, four or more different average weights.

The granules may be cut in a very large liquid-filled chamber, in which the granules are also cooled. In some embodiments the cooling is combined with transfer of the granules away from the chamber. This can be done e.g. by cooling the cut granules in water during transfer from the liquid filled chamber to a de-watering device. The transfer time from cutting to de-watering can be less than 6 s. The advantage of this is that water-soluble ingredients in the gum composition are not unnecessarily washed out of the granules. Optionally, the total time of contact between granules and cooling water can be further limited to less than 4 s.

In some embodiments the chewing gum composition fed to the extruder is a gum base, and that it at least includes one or more flavouring agents when extruded through the die means. The flavours within the granules cause a prolonged release of taste during mastication.

The powdered chewing gum tablet base material according to the invention may for example comprise so-called primary particles or aggregated primary particles, also referred to as granules. When these are compressed, bonds are established between the particles or granules, thereby conferring a certain mechanical strength to the compressed chewing gum tablet.

It should be noted that the above-introduced terms: powder, primary particles and granules may be somewhat misleading in the sense that the difference between primary particles and granules may very often be looked upon differently depending on the background of the user. Some may for instance regard a sweetener, such as sorbitol, as a primary particle in spite of the fact that sorbitol due to the typically preprocessing performed on sorbitol when delivered to the customer should rather be regarded as some sort of granule. The definition adopted in the description of this invention is that granules refer to macro-particles comprising more or less preprocessed primary particles.

When pressure is applied to the powder raw material, the bulk volume is reduced and the amount of air is decreased. During this process energy is consumed. As the particles come into closer proximity to each other during the volume reduction process, bonds may be established between the particles or granules. The formation of bonds is associated with a reduction in the energy of the system as energy is released.

Volume reduction takes place by various mechanisms and different types of bonds may be established between the particles or granules depending on the pressure applied and the properties of the particles or granules.

Examples of gum base granulate usable for chewing gums of the present invention are described in the PCT/DK02/

00461 and PCT/DK02/00462, hereby incorporated by reference. Chewing gum base formulations may comprise one or more elastomeric compounds of synthetic origin selected from polyisobutylene, isobutylene-isoprene copolymer, styrene-butadiene copolymers, polyvinyl acetate, polyisoprene, polyethylene and vinyl acetate-vinyl burate copolymer, and typically one or more resinous compounds which may be of synthetic or natural origin, fillers, softening compounds and minor amounts of miscellaneous ingredients such as antioxidants and colorants, etc.

The composition of chewing gum base formulations, which are admixed with chewing gum ingredients as defined below, can vary substantially depending on the particular product to be prepared and on the desired masticatory and other sensory characteristics of the final product. However, typical ranges (weight %) of the above gum base components are: 5 to 50% by weight elastomeric compounds, 5 to 55% by weight elastomer plasticizers, 0 to 50% by weight filler/texturiser, 5 to 35% by weight softener and 0 to 1% by weight of miscellaneous ingredients such as antioxidants, colorants, etc.

Gum base granulates may be manufactured according to conventional methods or e.g. those described in the PCT/DK02/00461 and PCT/DK02/00462, hereby incorporated by reference.

In the present context, chewing gum tablet base material may include bulk sweeteners, high intensity sweeteners, flavoring agents, softeners, emulsifiers, coloring agents, binding agents, acidulants, fillers, antioxidants and other components that confer desired properties to the finished chewing gum tablet.

Suitable bulk sweeteners include e.g. both sugar and non-sugar components. Bulk sweeteners typically constitute from about 5 to 95% by weight of the chewing gum tablet, more typically about 20 to 80% by weight such as 30 to 60% by weight of the chewing gum tablet. Useful sugar sweeteners are saccharide-containing components commonly known in the tablet and chewing gum tablet art including, but not limited to, sucrose, dextrose, maltose, dextrins, trehalose, D-tagatose, dried invert sugar, fructose, levulose, galactose, corn syrup solids, and the like, alone or in combination.

If a low calorie gum is desired, a low calorie bulking agent can be used. Examples of low calorie bulking agents include polydextrose, Raftilose, Raftilin, Inuline, fructooligosaccharides (NutraFlora®, palatinose oligosaccharided; guar gum hydrolysates (e.g. Sun)Fiber® or indigestible dextrins (e.g. Fibersor). However, other low calorie-bulking agents can be used.

Further chewing gum tablet base material ingredients, which may be included in the chewing gum tablet mixture processed in the present process, include surfactants and/or solubilisers. As examples of types of surfactants to be used as solubilisers in a chewing gum composition, according to the invention reference is made to H.P. Fiedler, Lexikon der Hilfstoffe für Pharmacie, Kosmetik and Angrenzende Gebiete, pages 63-64 (1981) and the lists of approved food emulsifiers of the individual countries. Anionic, cationic, amphoteric or non-ionic solubilisers can be used. Suitable solubilisers include lecithins, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilisers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllactylate, sodium laurylsulfate, polyoxyethylated hydrogenated castor oil, blockcopolymers of ethylene oxide and propyleneoxide and polyoxyethylene fatty alcohol ether. The solubiliser may either be a single compound or a combination of several compounds. The expression "solubiliser" is used in the present text to describe both possibilities; the solubiliser used must be suitable for use in food and/or medicine.

Aroma agents and flavoring agents which are useful in a chewing gum produced by the present process are e.g. natural and synthetic flavorings (including natural flavorings) in the form of freeze-dried natural vegetable components, essential oils, essences, extracts, powders, including acids and other substances capable of affecting the taste profile. Examples of liquid and powdered flavorings include coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In one embodiment, the flavor is one or more natural flavoring agent(s) which is/are freeze-dried, for example in the form of a powder, slices or pieces of combinations thereof. The particle size of such agent may be less than 3 mm, such as less than 2 mm, such as less than 1 mm, and calculated as the longest dimension of the particle. The natural flavoring agent may also be in a form where the particle size is from about 3 µm to 2 mm, such as from 4 µm to 1 mm. Examples of natural flavoring agents include seeds from a fruit e.g. from strawberry, blackberry and raspberry.

Various synthetic flavors, such as mixed fruit flavor may also be used according to the present invention. As indicated above, the aroma agent may be used in quantities smaller than those conventionally used. The aroma agents and/or flavors may be used in an amount from 0.01 to about 30% by weight of the final product depending on the desired intensity of the aroma and/or flavor used. For example, the content of aroma/flavor may be in the range of from 0.2 to 3% by weight of the total composition.

The gum base formulations applicable within the scope of the invention comprise a synthetic elastomer selected from polyisobutylene. e.g. having a gas pressure chromatography (GPC) average molecular weight in the range of about 10,000 to 1,000,000 including the range of 50,000 to 80,000, isobutylene-isoprene copolymer (butyl elastomer), styrene-butadiene copolymers e.g. having styrene-butadiene ratios of about 1:3 to 3:1, polyvinyl acetate (PVA), e.g. having a GPC average molecular weight in the range of 2,000 to 90,000 such as the range of 3,000 to 80,000 including the range of 30,000 to 50,000, where the higher molecular weight polyvinyl acetates are typically used in bubble gum base, polyisoprene, polyethylene, vinyl acetate-vinyl laurate copolymer e.g. having a vinyl laurate content of about 5 to 50% by weight such as 10 to 45% by weight of the copolymer, and combinations hereof. It is common in the industry to combine in a gum base a synthetic elastomer having a high molecular weight and a low molecular weight elastomer. Presently preferred combinations of synthetic elastomers include, but are not limited to, polyisobutylene and styrene-butadiene, polyisobutylene and polyisoprene, polyisobutylene and isobutylene-isoprene copolymer (butyl rubber) and a combination of polyisobutylene, styrene-butadiene copolymer and isobutylene isoprene copolymer, and all of the above individual synthetic polymers in admixture with polyvinyl acetate, vinyl acetate-vinyl laurate copolymers, respectively and mixtures thereof. Particularly interesting elastomeric or resinous polymer compounds which advantageously can be used in a process according to the invention include polymers which, in contrast to currently used elastomers and resins, can be degraded physically, chemically or enzymatically in the environment after use of the chewing gum, thereby giving rise to less environmental pollution than chewing gums based on non-degradable polymers, as the used degradable chewing gum remnants will eventually disintegrate and/or can be removed more readily by physical or chemical means from the site where it has been dumped.

In the present context, useful elastomer plasticizers include, but are not limited to, natural rosin esters, often referred to as ester gums including as examples glycerol esters of partially hydrogenated rosins, glycerol esters of polymerised rosins, glycerol esters of partially dimerised rosins, glycerol esters of tally oil rosins, pentaerythritol esters of partially hydrogenated rosins, methyl esters of rosins, partially hydrogenated methyl esters of rosins and pentaerythritol esters of rosins. Other useful resinous compounds include synthetic resins such as terpene resins derived from alpha-pinene, beta-pinene, and/or d-limonene, natural terpene resins; and any suitable combinations of the foregoing. The choice of elastomer plasticizers will vary depending on the specific application, and on the type of elastomer(s) being used.

EXAMPLES

Example 1—Preparation of a Complex Comprising THC

A. Preparation of a Complex Comprising THC and Ambersep 900 on OH-Form (15% Loading)

882 gram of THC is dissolved in 88 L ethanol and to the stirred solution is added 5 kg of Ambersep 900 on OH-form as ion exchange resin. When all THC has been bound by the ion exchange resin the pressure was reduced and the obtained mixture is concentrated in vacuo at elevated temperature affording the desired complex as a powder.

B. Preparation of a Complex Comprising THC and Ambersep 900 on OH-Form (12% Loading) Including Glycerin 882 gram of THC is dissolved in 88 L ethanol. To the stirred solution is added 5 kg of Ambersep 900 on OH-form as ion exchange resin. When all THC has been bound by the ion exchange resin, a solution of 1.47 kg glycerin in 1.2 L of ethanol was added. The obtained mixture is stirred for e.g. 30 min and then the pressure was reduced and the obtained mixture is concentrated in vacuo at elevated temperature affording the desired complex as a powder.

C. Preparation of a Complex Comprising THC and Cholestyramine on Cl-Form (15% Loading)

882 gram of THC is dissolved in 88 L of ethanol. To the stirred solution is added 112 g of NaOH. The obtained mixture was stirred until all THC has been deprotonated. Afterwards 5 kg Cholestyramine on Cl-form as ion exchange resin was added. When all THC has been bound by the ion exchange resin the pressure was reduced and the obtained mixture is concentrated in vacuo at elevated temperature affording the desired complex as a powder.

D. Preparation of a Complex Comprising THC and Cholestyramine on Cl-Form (12% Loading) Including Glycerin 882 gram of THC is dissolved in 88 L of ethanol and to the stirred solution is added 112 g of NaOH. The obtained mixture was stirred until all THC has been deprotonated and afterwards was added 5 kg of Cholestyramine on Cl-form as ion exchange resin. When all THC has been bound by the ion exchange resin, a solution of 1.47 kg of glycerin in 1.2 L of ethanol was added. The obtained mixture is stirred for e.g. 30 min and then the pressure was reduced and the obtained mixture is concentrated in vacuo at elevated temperature affording the desired complex as a powder.

TABLE 1

Composition of complexes A-D. The type of ion exchange resin used is given above, under corresponding sections A-D.

| Complex | Amount | | | | | |
| --- | --- | --- | --- | --- | --- | --- |
| | THC (gram) | Ethanol for THC (Liter) | NaOH (gram) | Ion exchange resin (kg) | Glycerin (kilogram) | Ethanol for glycerin (Liter) |
| A | 882 | 88 | — | 5 | — | — |
| B | 882 | 88 | — | 5 | 1.47 | 1.2 |
| C | 882 | 88 | 112 | 5 | — | — |
| D | 882 | 88 | 112 | 5 | 1.47 | 1.2 |

It should be noted that alternatively, the complexes C and D may be filtered in order to remove formed sodium chloride. Removing sodium chloride may decrease the need for taste masking, which would often be employed when no filtering is used in order to mask the salty taste of sodium chloride.

It should be noted that alternatively, the ion exchange resin may be added to the ethanol first, after which the cannabinoid(s) is added. However, it may be advantageous to use a fraction, e.g. about 10% of the ethanol, to premix with the cannabinoid(s) in order to facilitate a fast and effective mixing.

As demonstrated above, a cannabinoid comprising complex may be obtained in a number of different ways. However, it should be noted that if the obtained complex is not compressible, it may be necessary to include further compression enhancers in the powdered composition, depending on the specific intended use e.g. in an orally dispensable delivery vehicle, or the powdered composition may be made compressible by means of inclusion into a compressible powder, such as the remaining ingredients for the orally dispensable delivery vehicle.

However, it may in such cases where the obtained complex has a lowered compressibility be advantageous to ensure a higher loading of the basic ion exchange resin with the cannabinoid, i.e. to increase the ratio of cannabinoid to basic ion exchange resin.

Example 2—Preparation of a Complex Comprising THC and CBD

F. Preparation of a Complex Comprising THC and CBD and Ambersep 900 on OH-Form (15% Loading)

441 g of THC and 441 g of CBD are dissolved in 88 L ethanol and to the stirred solution is added 5 kg of Ambersep 900 on OH-form as ion exchange resin. When all THC and CBD have been bound by the ion exchange resin the pressure was reduced and the obtained mixture is concentrated in vacuo at elevated temperature affording the desired complex as a powder.

G. Preparation of a Complex Comprising THC and CBD and Ambersep 900 on OH-Form (15% Loading) Including Glycerin 441 g of THC and 441 g of CBD are dissolved in 88 L of ethanol and to the stirred solution is added 5 kg of Ambersep 900 on OH-form as ion exchange resin. When all THC has been bound by the ion exchange resin, a solution of 1.47 kg of glycerin in 1.2 L of ethanol was added. The obtained mixture is stirred for e.g. 30 min and then the pressure was reduced and the obtained mixture is concentrated in vacuo at elevated temperature affording the desired complex as a powder.

TABLE 2

Composition of complexes F-G. The type of ion exchange resin used is given above, under corresponding sections F-G.

| Complex No. | THC (gram) | CBD (gram) | Ethanol for Cannabinoids (Liter) | Ion exchange resin (kg) | Glycerin (kilogram) | Ethanol for glycerin (Liter) |
|---|---|---|---|---|---|---|
| F | 441 | 441 | 88 | 5 | — | — |
| G | 441 | 441 | 88 | 5 | 1.47 | 1.2 |

H. Change Counter Ion from Cl-Form to OH-Form

In an appropriate mixer or column charged with an appropriate solvent or mixtures of solvent (e.g. water, methanol/water, ethanol/water) is added ion exchange resin on Cl-form. This mixture is treated with a mineral base (e.g. NaOH, KOH, LiOH) in excess relative to the loading capacity of the basic ion exchange resin. The obtained mixture is stirred for a given period of time, then filtered and subsequent washed with water until pH of the wash water is neutral. The residue is then transferred to an appropriate mixer charged with an appropriate solvent or mixture of solvent (e.g. methanol/water, ethanol/water) is added cannabinoid/cannabinoids. Subsequent is added an ion exchange resin and after being stirred for at certain period of time, pressure is reduced in the mixer to remove solvent and heat may be applied affording a dry powder with a cannabinoid loading of approx. 5% to 95% of the loading capacity for the ion exchange resin used. Alternatively the obtained mixture can be filtered and the dried under vacuum.

Example 3—Preparation of Cannabinoid Containing Lozenges

Cannabinoid lozenges; C-lozenge I, C-lozenge II, having the components of Table 3 were formed using the process as described below:

Granulation Stage

1. Mannitol was mixed with intragranular portion of hydroxypropyl methylcellulose (HPMC) and potassium acesulfame for 10 min at low impeller speed, followed by the addition of purified water and mixed at low chopper and slow impeller to achieve the ampere reading of 15-17 AMP (considered the end point for wet granulation).

2. Post granulation drying in fluidized bed dryer (FBD) at 50-60 degrees Celsius was performed until the loss on drying (LOD) was between 2-2.5%.

3. Granulates were sifted and milled to pass them though 20#ASTM mesh.

Blending Stage

4. The extragranular materials i.e. cannabinoid complex, citric acid, flavors, sweeteners and extra granular portion of HPMC were sifted through 20#ASTM mesh.

5. Intragranular components and extragranular components were blended in double cone blender at 12 rpm for 30 min.

Lubrication Stage

6. The post blending component was then blended with magnesium stearate for 5 min.

Compression 7. 1200 mg lozenges were compressed on D tooling tablet press keeping hardness range of 90±20 N where the main compression force was between 15-20 kN and precompression force was between 1.5 to 2.5 kN with the friability range of NMT 0.8%.

TABLE 3

Composition of cannabinoid containing lozenges C-Lozenge I and C-Lozenge II.

| | | C-Lozenge I | | C-Lozenge II | |
|---|---|---|---|---|---|
| S. No. | Raw Material Name | Amount (% w/w) | Amount (mg/Lozenge) | Amount (% w/w) | Amount (mg/Lozenge) |
| | Intragranular Stage | | | | |
| 1 | Mannitol (Pearlitol 160 C) USP | 74.5 | 894.2 | 78.6 | 942.7 |
| 2 | Metolose 90 SH 4000 cps SR USP | 4.8 | 57.8 | 4.9 | 58.6 |
| 3 | Metolose 90 SH 100 cps SR USP | 4.8 | 57.8 | 4.9 | 58.6 |
| 4 | Potassium Acesulfame USP | 0.3 | 3.6 | 0.3 | 3.6 |
| 5 | Purified Water IP | qs | qs | qs | qs |

TABLE 3-continued

Composition of cannabinoid containing lozenges C-Lozenge I and C-Lozenge II.

|  |  | C-Lozenge I | | C-Lozenge II | |
|---|---|---|---|---|---|
| S. No. | Raw Material Name | Amount (% w/w) | Amount (mg/Lozenge) | Amount (% w/w) | Amount (mg/Lozenge) |
| | | Extragranular State | | | |
| 6a | THC complex B from example 1 | 6.9 | 83.3 | — | — |
| 6b | THC-CBD complex F from example 2 | — | — | 5.6 | 66.7 |
| 7 | Metolose 90 SH 100 cps SR USP | 4.8 | 57.8 | 2.0 | 23.4 |
| 8 | Aspartame USP | 1.1 | 13.4 | 1.1 | 13.6 |
| 9 | Citric acid | 0.4 | 5.0 | 0.4 | 5.0 |
| 10 | Flavor ultraseal 151 Peppermint IH | 1.2 | 13.9 | 1.2 | 14.1 |
| | | Lubrication Stage | | | |
| 11 | Magnesium Stearate IP | 1.1 | 13.4 | 1.1 | 13.6 |
| | Total | 100 | 1200 | 100 | 1200 |

It should be noted that alternatively lozenges may be obtained via direct compression techniques where directly compressible ingredients are used instead of using granulates as shown above.

Example 4—Fast Dissolving Granulation

Compositions of Fast Dissolving Granulations. In these compositions, the water soluble excipient is a saccharide. As described above, the tablets of the invention may be formulated by a method wherein a fast dissolving granulation, comprising a low melting point compound and a water soluble excipient, is mixed separately from other tablet constituents. A portion of the fast dissolving granulation may then be combined with the other tablet constituents. In this example, several specific examples of fast dissolving granulations are set forth, the compositions of which are shown in table 4.

TABLE 4

Composition of fast dissolving granulation formulations
Fast dissolving granulation formulations.

| Fast Dissolving Granulation Composition | Low Melting Point Compound (amount) | Saccharide (amount) |
|---|---|---|
| 1 | Wecobee M hydrogenated vegetable oil (1 Kg) | mannitol powder (5 Kg) |
| 2 | Gelucire 33/01 semisynthetic glycerides (200 g) | mannitol powder (1 Kg) |
| 3 | Wecobee M (150 g) | crystalline maltose (100 g) mannitol powder (750 g) |
| 4 | Polyethylene glycol900 (100 g) | Fructose powder (400 g) |

Fast dissolving granulations 1 and 2 were prepared by heating the low melting point compound to 50 degrees Celsius. At 50 degrees Celsius, Wecobee M and Gelucire 33/01 become molten. The molten material was gradually added to the mannitol powder in a high shear granulator (Diosna). The granulation was mixed at high speed. When the granulation end point was reached as determined by visual inspection, the granulation was allowed to congeal. The congealed granulation was then milled using a CoMill.

Granulation 3 was granulated by combining melted Wecobee M with the maunitol in a high shear mixer (Robot Coupe) and blending until the granules formed. Granulation 4 was made by combining the melted PEG with fructose powder in a planetary mixer (low shear mixer) and mixing until the granules formed. The granulations were allowed to cool, then were screened.

Example 5—Fast Dissolving Cannabinoid Tablets (FDCT)

The following is an example of a fast dissolving tablet comprising cannabinoid.

TABLE 5

Composition of Fast Dissolving Cannabinoid Tablets FDCT-I and FDCT-II

|  | FDCT-I | | FDCT-II | |
|---|---|---|---|---|
| Ingredient | Amount (mg tablet) | Content (% w/w) | Amount (mg tablet) | Content (% w/w) |
| THC complex B | 83.3 | 13.9 | — | — |
| THC-CBD complex F | — | — | 66.7 | 11.1 |
| Citric acid | 10.0 | 1.7 | 10.0 | 1.7 |
| Magnasweet 135 (sweetening agent) | 3.8 | 0.6 | 3.9 | 0.7 |
| Aspartame (sweetening agent) | 6.3 | 1.1 | 6.5 | 1.1 |
| Flavoring agent | 7.6 | 1.3 | 7.8 | 1.3 |
| Crosscarmellose sodium (disintegrant) | 38.0 | 6.3 | 39.2 | 6.5 |
| Silicone dioxide (glidant flow aid) | 1.9 | 0.3 | 2.0 | 0.3 |
| Magnesium stearate (lubricant) | 3.2 | 0.5 | 3.3 | 0.5 |
| Fast dissolving granulation 4 of example 4 | 445.9 | 74.3 | 460.6 | 76.8 |
| Total | 600.0 | 100.0 | 600.0 | 100.0 |

Ingredients as indicated in table 5 were screened, then mixed in a V-blender. Tablets were compressed using a hydraulic press (Carver Press) at 600 lb (about 2.7 kN). The tablets had a hardness of 0.2-0.5 kP and disintegrated in less than 15 seconds.

Example 6—Preparation of Gum Base by Continuous Extrusion

The composition of gum bases are presented in Table 6.

TABLE 6

Gum base composition GB1. Amounts are given in wt-% of the gum base.

| Ingredient | Amount (% w/w) |
|---|---|
| Elastomer | 15 |
| Gum resins | 20 |
| Synthetic resins | 15 |
| Filler | 25 |
| Plasticizers | 15 |
| Emulsifier | 10 |
| Antioxidant | 0.1 |

GB = Gum Base.

A gum base composition in the form of pellets was fed directly to an extruder in a first opening.

The gum base pellets were fed individually to the extruder (Leistrits ZSE/BL 360 kw 104, available from GALA GmbH, Germany). The resulting composition was extruded to a granulator comprising a die plate and a water-filled chamber (granulator A5 PAC 6, GALA GmbH, Germany) connected to a water system comprising a water supply for the granulator and centrifugal dryer (TWS 20, available from GALA GmbH, Germany).

The gum base composition GB1 of Table 6 was fed to the extruder with a feed rate of 250 kg/h and an extruder screw speed of 200 rpm. The gum base compositions were made in separate productions. The temperature in the composition at the feed end of the extruder was 100 degrees Celsius and the temperature of the composition at the outlet of the extruder was 109 degrees Celsius. The composition was delivered by the extruder device to the inlet side of a die plate at a pressure of 36 bar. The composition was extruded through the die plate having a temperature of 200 degrees Celsius and 1100 holes of a diameter of 0.3 mm. In the granulator chamber the extruded composition was cut to granules by a cutter with 13 blades mounted in star shape on a central axle rotating with a cutter speed of 2800 rpm. The granules were cooled and transported to the centrifugal dryer in water with a temperature of 17 degrees Celsius and a flow rate of 22 m³/h. The average cooling and transport time in water was approx. 90 seconds. The individual granules had an average weight of 0.002 g.

Example 7—Preparation of Compressed Chewing Gum

The compositions of compressed chewing gums CG1 and CG2 are presented in Table 7.

TABLE 7

Compressed chewing gum composition. Amounts are given in wt-% of the chewing gum formulation.

| | CG1 | | CG2 | |
|---|---|---|---|---|
| Ingredient | Amount (mg tablet) | Content (% w/w) | Amount (mg tablet) | Content (% w/w) |
| GB1 | 621.1 | 31.1 | 626.5 | 31.3 |
| Sorbitol | 417.3 | 20.9 | 420.9 | 21.0 |
| Acesulfame K | 1.9 | 0.1 | 2.0 | 0.1 |
| Aspartame | 3.9 | 0.2 | 3.9 | 0.2 |
| THC complex B | 83.3 | 4.2 | — | — |
| THC-CBD complex F | — | — | 66.7 | 3.3 |
| Citric acid | 5.0 | 0.25 | 5.0 | 0.25 |
| Flavor | 29.1 | 1.5 | 29.4 | 1.5 |
| Xylitol | 838.4 | 41.9 | 845.7 | 42.3 |
| Total | 2000.0 | 100.0 | 2000.0 | 100.0 |

The gum base granules obtained in Example 3 (GB1) were individually mixed in a standard mixer with tablet base material in the form of powder as outlined in Table 7.

Before pressing, the gum base granules with the tablet base material in the form of powder, the gum base granules passed a standard horizontal vibration sieve for removing any particles larger than 1.3 mm.

The chewing gum composition CG1 and CG2, respectfully, was subsequently conveyed to a rotary tablet pressing machine (Hata tablet press) comprising dosing apparatus. About 2 g of the chewing gum composition CG1 and CG2, respectfully, was added and slightly pressed into compressed chewing gum CG1 and CG2, respectfully. The force in this pre-pressing step was about 33.0-33.6 kN. The tablet was ejected. The samples CG1 and CG2 were produced individually.

Alternatively, a two-module chewing gum tablet, such as a two-layer chewing gum tablet, may be made. About 1 g of a first powdered portion of chewing gum composition (Table 7) is added and slightly pressed into a first pressed material of about 1 g. The force in this pre-pressing step is about 10 kN. Thereafter a second powdered portion of chewing gum composition (Table 7) is added (1 g) to the punch die fully covering the capsule in the punch die. The main pressing is performed with a force about 33.0-33.6 kN. The tablet is ejected. A two-module chewing gum tablet may also be made, where the first and second modules have different composition, e.g. one comprising gum base and one free of gum base. The content of the cannabinoid comprising complex may also be set to a different level for each layer. Also, two different cannabinoid comprising complexes according to the invention may be used for each module, or even for the same module; e.g. in order to use different cannabinoids for each complex, or a different loading degree for each complex.

The invention claimed is:
1. A cannabinoid chewing gum tablet comprising:
   a gum base portion comprising water-insoluble gum base ingredients, including natural resins in a range of 8 to 45% by weight of the gum base portion;
   a bulk portion comprising bulk sweeteners in an amount of 30 to 70% by weight of the cannabinoid chewing gum tablet; and
   a powdered composition comprising a complex between one or more cannabinoids having at least one phenolic moiety and a basic ion exchange resin, wherein said one or more cannabinoids is present in an amount of at least 1 percent by weight of the powdered composition, the one or more cannabinoids being present in the cannabinoid chewing gum tablet in an amount of between 1 and 400 milligrams.

2. The cannabinoid chewing gum tablet according to claim 1, wherein the basic ion exchange resin comprises a strongly basic ion exchange resin.

3. The cannabinoid chewing gum tablet according to claim 1, wherein the basic ion exchange resin comprises a weakly basic ion exchange resin.

4. The cannabinoid chewing gum tablet according to claim 1, wherein the basic ion exchange resin comprises cross-linked polystyrene.

5. The cannabinoid chewing gum tablet according to claim 1, wherein the basic ion exchange resin comprises a styrene-divinylbenzene copolymer.

6. The cannabinoid chewing gum tablet according to claim 1, wherein a loading of the basic ion exchange resin is between 5 percent and 95 percent.

7. The cannabinoid chewing gum tablet according to claim 1, wherein the powdered composition comprises at least two cannabinoids.

8. The cannabinoid chewing gum tablet according to claim 1, wherein the one or more cannabinoids is derived from cannabis.

9. The cannabinoid chewing gum tablet according to claim 1, wherein the one or more cannabinoids comprises THC.

10. The cannabinoid chewing gum tablet according to claim 1, wherein the one or more cannabinoids comprises CBD.

11. The cannabinoid chewing gum tablet according to claim 1, wherein the one or more cannabinoids is selected from cannabinoids having the following structure

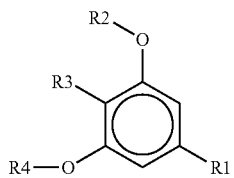

where R1 is an alkyl comprising at least 4 carbons and having a longest chain of at least 4 carbons,
where R2 is selected from hydrogen, hydrocarbon, and functionalized hydrocarbon,
where R3 is a hydrocarbon, and functionalized hydrocarbon,
where R4 is selected from hydrogen, hydrocarbon, and functionalized hydrocarbon,
where at least one of R2 and R4 is hydrogen,
where R2 or R4 may be connected to R3 to form R2-R3 or R4-R3, respectfully.

12. The cannabinoid chewing gum tablet according to claim 1, wherein the powdered composition comprises one or more aid substance(s) in amounts of between 1 and 70 percent by weight of the powdered composition.

13. The cannabinoid chewing gum tablet according to claim 1, wherein the powdered composition comprises said complex in an amount of between 30 and 100 percent by weight of the powdered composition.

14. The cannabinoid chewing gum tablet according to claim 1, wherein an average particle size of the powdered composition is between 1 and 400 micrometers.

15. A method of alleviation of pain, by administering an effective amount of the cannabinoid chewing gum tablet according to claim 1.

16. A method of mitigation of appetite deficiency by administering an effective amount of the cannabinoid chewing gum tablet according to claim 1.

17. A compressed cannabinoid chewing gum tablet comprising:
gum base granules comprising water-insoluble gum base ingredients, including elastomers in a range of 5 to 40% by weight of the gum base granules;
a bulk portion comprising bulk sweeteners in an amount of 20 to 80% by weight of the compressed cannabinoid chewing gum tablet; and
a powdered composition comprising a complex between one or more cannabinoids having at least one phenolic moiety and a basic ion exchange resin,
the one or more cannabinoids being present in the compressed cannabinoid chewing gum tablet in an amount of between 1 and 400 milligrams.

18. A cannabinoid lozenge tablet comprising:
a diluent portion present in an amount of 500 to 1100 mg per cannabinoid lozenge tablet;
one or more excipients selected from the group consisting of taste masking agents, antioxidants, glidants, colorant, and combinations thereof; and
a powdered composition comprising a complex between one or more cannabinoids having at least one phenolic moiety and a basic ion exchange resin,
the one or more cannabinoids being present in the cannabinoid lozenge tablet in an amount of between 1 and 400 milligrams.

19. The cannabinoid lozenge tablet according to claim 18, wherein the powdered composition comprises said complex in an amount of between 30 and 100 percent by weight of the powdered composition.

20. A fast dissolving cannabinoid tablet comprising:
a soluble excipient present in an amount of 25 to 97.5% by weight of the fast dissolving cannabinoid tablet;
one or more excipients selected from the group consisting of taste masking agents, antioxidants, glidants, colorant, and combinations thereof; and
a powdered composition comprising a complex between one or more cannabinoids having at least one phenolic moiety and a basic ion exchange resin,
the one or more cannabinoids being present in the fast dissolving cannabinoid tablet in an amount of between 1 and 400 milligram.

21. The fast dissolving cannabinoid tablet according to claim 20, wherein the basic ion exchange resin comprises a strongly basic ion exchange resin.

* * * * *